Figure 1:
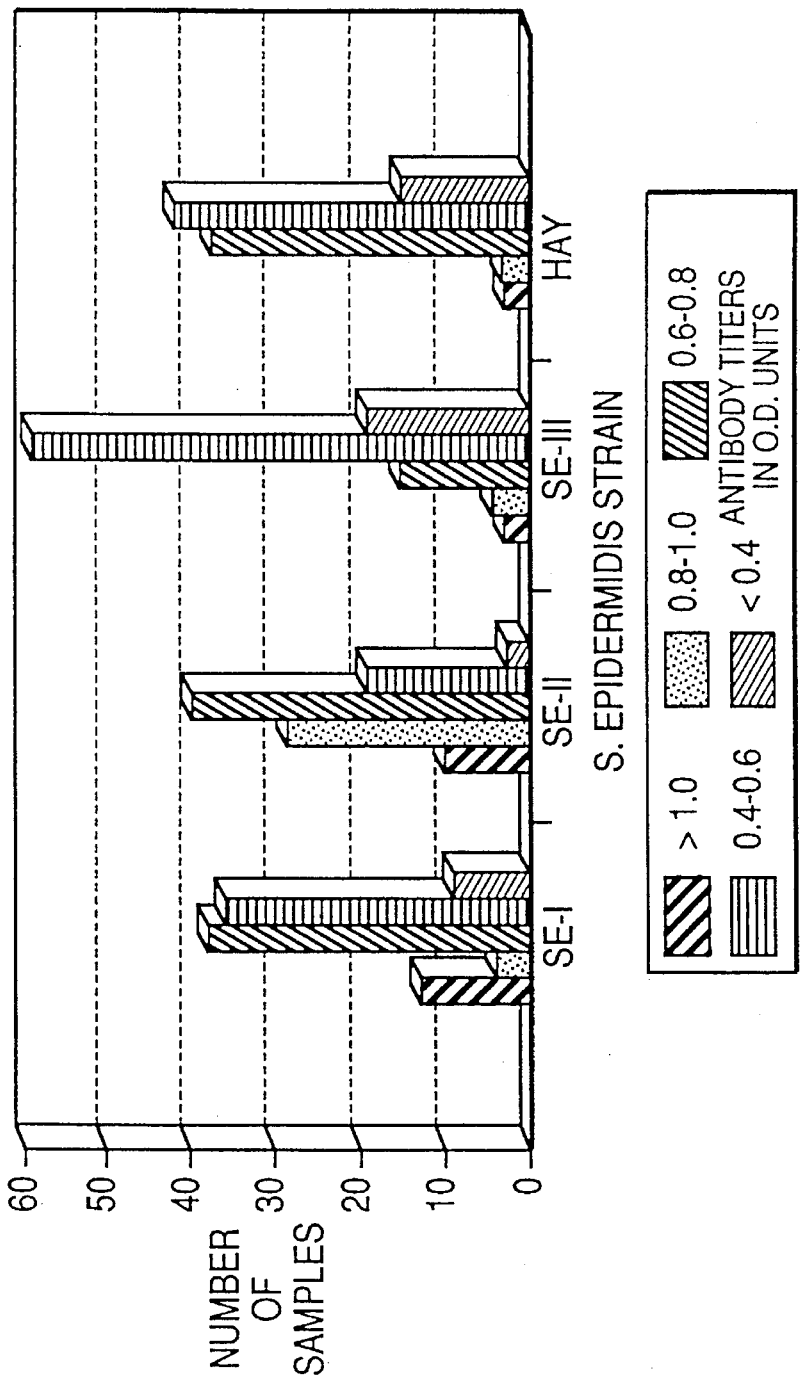

US005571511A

United States Patent [19]

Fischer

[11] Patent Number: 5,571,511
[45] Date of Patent: Nov. 5, 1996

[54] BROADLY REACTIVE OPSONIC ANTIBODIES THAT REACT WITH COMMON STAPHYLOCOCCAL ANTIGENS

[75] Inventor: Gerald W. Fischer, Bethesda, Md.

[73] Assignee: The U.S. Government, Washington, D.C.

[21] Appl. No.: 219,238

[22] Filed: Mar. 28, 1994

Related U.S. Application Data

[63] Continuation of Ser. No. 854,027, Mar. 19, 1992, abandoned, which is a continuation-in-part of Ser. No. 804,317, Feb. 25, 1992, abandoned, which is a continuation of Ser. No. 601,089, Oct. 22, 1990, abandoned.

[51] Int. Cl.$^6$ ..................................................... A61K 39/40
[52] U.S. Cl. .................................. 424/165.1; 424/130.1; 424/164.1; 424/237.1; 435/7.33; 435/252.8; 435/822
[58] Field of Search ........................... 424/165.1, 164.1; 435/7.33, 68.1, 822, 252.8, 2; 436/542; 514/54

[56] References Cited

U.S. PATENT DOCUMENTS

| 4,027,010 | 5/1977 | Kiseley et al. | |
|---|---|---|---|
| 4,197,290 | 4/1980 | Yoshida . | |
| 4,425,330 | 1/1984 | Norcross et al. | 424/92 |
| 5,505,945 | 4/1996 | Gristina et al. | 424/164.1 |

OTHER PUBLICATIONS

Yang et al., "Mechanisms of Bacterial Opsonization by Immune Globulin Intravenous: Correlation of Complement Consumption with Opsonic Activity and Protective Efficacy," *The Journal of Infectious Diseases*, 159:701–707 (1989).

Fischer et al., "Therapeutic Uses of Intravenous Gammaglobulin for Pediatric Infections," *Pediatric Clinics of North America*, 35:517–533 (1988).

Bronswijk et al., "Heterogeneity In Opsonic Requirements Of *Staphylococcus epidermidis*: Relative Importance Of Surface Hydrophobicity, Capsules and Slime," *Immunology*, pp. 67:81–86 (1989).

I. W. Sutherland, "Separation and Purification Of Bacterial Antigens," *Handbook of Experimental Immunology*, D. M. Weir, ed., chapter 2, pp. 2.1–2.17 (1978).

Naumova et al., "The Occurrence of Teichoic Acids in *Streptomycetes*," *Chemical Abstracts*, 93, Abstract No. 3555r (1980).

Espersen et al., "*Staphylococcus Aureus*," pp. 127–134 in *Antigen Detection to Diagnose Bacterial Infections*, vol. 2, (CRC Press, Inc., Boca Raton, Florida, 1986).

A. Fattom et al., Capsular Polysaccharide Serotyping Scheme for *Staphylococcus epidermidis*, *Journal of Clinical Microbiology*, vol. 30, No. 12, pp. 3270–3273 (Dec. 1992).

K. Yoshida et al., Cross Protection Between a Strain of *Staphylococcus epidermidis* and Eight Other Species of Coagulase–Negative Staphylococci, Can. J. Microbiol., vol. 34, pp. 913–915 (1988).

Fleer et al., "Septicemia due to Coagulase–negative Staphylococci in a Neonatal Intensive Care Unit: Clinical and Bacteriological Features and Contaminated Parenteral Fluids as a Source of Sepsis," *Pediatr. Infect. Dis.*, 2:426–431 (1983).

Fischer et al., "Diminished Bacterial Defenses with Intralipid," *The Lancet*, 2:819–820 (1980).

(List continued on next page.)

*Primary Examiner*—James C. Housel
*Assistant Examiner*—Ginny Allen Portner
*Attorney, Agent, or Firm*—Finnegan, Henderson, Farabow, Garrett & Dunner

[57] ABSTRACT

The invention relates to the identification, making, and isolation of immunoglobulin and antigen that is useful to prevent, diagnose, or treat Staphylococcus infections. The invention further relates to an in vivo animal model for testing the efficacy of pharmaceutical compositions, including the pharmaceutical compositions of immunoglobulin and isolated antigen described herein.

7 Claims, 12 Drawing Sheets

OTHER PUBLICATIONS

Yoshida et al., "Immunological Response to a Strain of *Staphylococcus epidermidis* in the Rabbit: Production of Protective Antibody," *J. Med. Microbiol.*, 11:371–377 (1978).

Yoshida et al., "Mouse Virulent Strain of *Staphylococcus epidermidis*," *Jap. J. Microbiol.*, 20:209–217 (1976).

West et al., "Detection of Anti–teichoic Acid Immunoglobulin G Antibodies in Experimental *Staphylococcus epidermidis* Endocarditis," *Infect. and Immun.*, 42:1020–1026 (1983).

Ichiman et al., "Protective Antibodies in Human Sera Against Encapsulated Strains of *Staphylococcus epidermidis*," *J. Applied Bacteriol.*, 63:165–69 (1987).

Espersen et al., "Enzyme–linked Immunosorbent Assay for Detection of *Staphylococcus epidermidis* Antibody in Experimental *S. epidermidis* Endocarditis," *J. Clin. Microbiol.*, 23:339–342 (1986).

T. Niizuma, "Passive Protective Activities of Specific Human Immuno–globulin Against Strain ST67P of *Staphylococcus Hyicus* Extracted from Pooled Human Sera," *Chem. Abstracts*, 115:181022v, p. 713 (1990).

T. Niizuma, "Passive Protection Activities of Specific Human Immunoglobulin Against Strain ST67P of *Staphylococcus Hyicus* Extracted from Pooled Human Sera," *St. Marianna Med. J.*, 18:940–946 (1990).

Certified English translation of document No. 10.

Espersen et al., "Solid Phase Radioimmunoassay for IgG Antibodies to *Staphylococcus epidermis*: use in Serious Coagulase–negative Staphylococcal Infections," *Arch. Intern. Med.*, 147:689–693 (1987).

Ichiman et al., "Protective Antibodies in Human Sera Against Encapsulated Strains of *Staphylococcus epidermidis*," *J. Appl. Bacteriol.*, 63:165–169 (1987).

Clark et. al., "Opsonic Activity of Intravenous Immunoglobulin Preparations Against *Staphylococcus epidermidis*," *J. Clin. Pathol.*, 39:856–860 (1986).

Clark et al., "Opsonic Requirements of *Staphylococcus epidermidis*," *J. Med. Microbiol.*, 22:1–7 (1986).

Fleer et al., "Opsonic Defense to *Staphylococcus epidermidis* in the Premature Neonate," *J. Infect. Dis.*, 152:930–937 (1985).

Ichiman et al., "Relation of Human Serum Antibody Against *Staphylococcus Epidermidis* Cell Surface Polysaccharide Detected by Enzyme–linked Immunosorbent Assay to Passive Protection in the Mouse," *J. Appl. Bacteriol.*, 71:176–181 (1991).

Ichiman et al., "Monoclonal IgM Antibody Protection in Mice Against Infection with an Encapsulated Strain of *Staphylococcus Epidermidis*," *Can. J. Microbiol.*, 37:404–407 (1991).

Fischer et al., "Directed Immune Globulin Enhances Survival in an Intralipid Induced Neonatal Model of Lethal *Staphylococcus Epidermidis* Sepsis," *Pediatr. Res.*, Abstract No. 1670, p. 281A (Apr. 1991).

C. C. Patrick, "Coagulase–negative Staphylococci: Pathogens with Increasing Clinical Significance," *J. of Pediatr.*, 116:497–507 (1990).

Freeman et al., "Association of Intravenous Lipid Emulsion and Coagulase–negative Staphylococcal Bacteremia in Neonatal Intensive Care Units," *New. Engl. J. Med.*, 323:301–308 (1990).

J. O. Klein, "From Harmless Commensal to Invasive Pathogen: Coagulase–negative Staphylococci," *New Engl. J. Med.*, 323:339–340 (1990).

Naumova et al, "The occurrence of teichoic acids in streptomycetes", Chem. Abstracts, 93(1): Abstract No. 3555r, p. 342 (Jul. 1980).

Yang et al, "Mechanisms of Bacterial Opsonization by Immune Globulin Intravenous: Correlation of Complement Consumption with Osonic Activity and Protective Efficacy", J. Inf. Dis, 159(4):701–709 (Apr. 1989).

G. W. Fischer, "Therapeutic Uses of Intravenous Gammaglobulin for Pediatric Infections", Pediatr Clin. North Am., 35(3):517–533 (Jun. 1988).

Van Bronswijk et al, "Heterogeneity in opsonic requirements of *Staphylococcus epidermidis*: relative importance of surface hydrophobicity, capsules and slime", Immunol. 67:81–86 (May 1989).

I. W. Sutherland "Separation and purification of bacterial antigens" in Handbook of Experimental Immunology, 3rd Ed., D. M. Weir, ed., pp. 2.1–2.17, Blackwell Scientific Publications (Oxford) (1978).

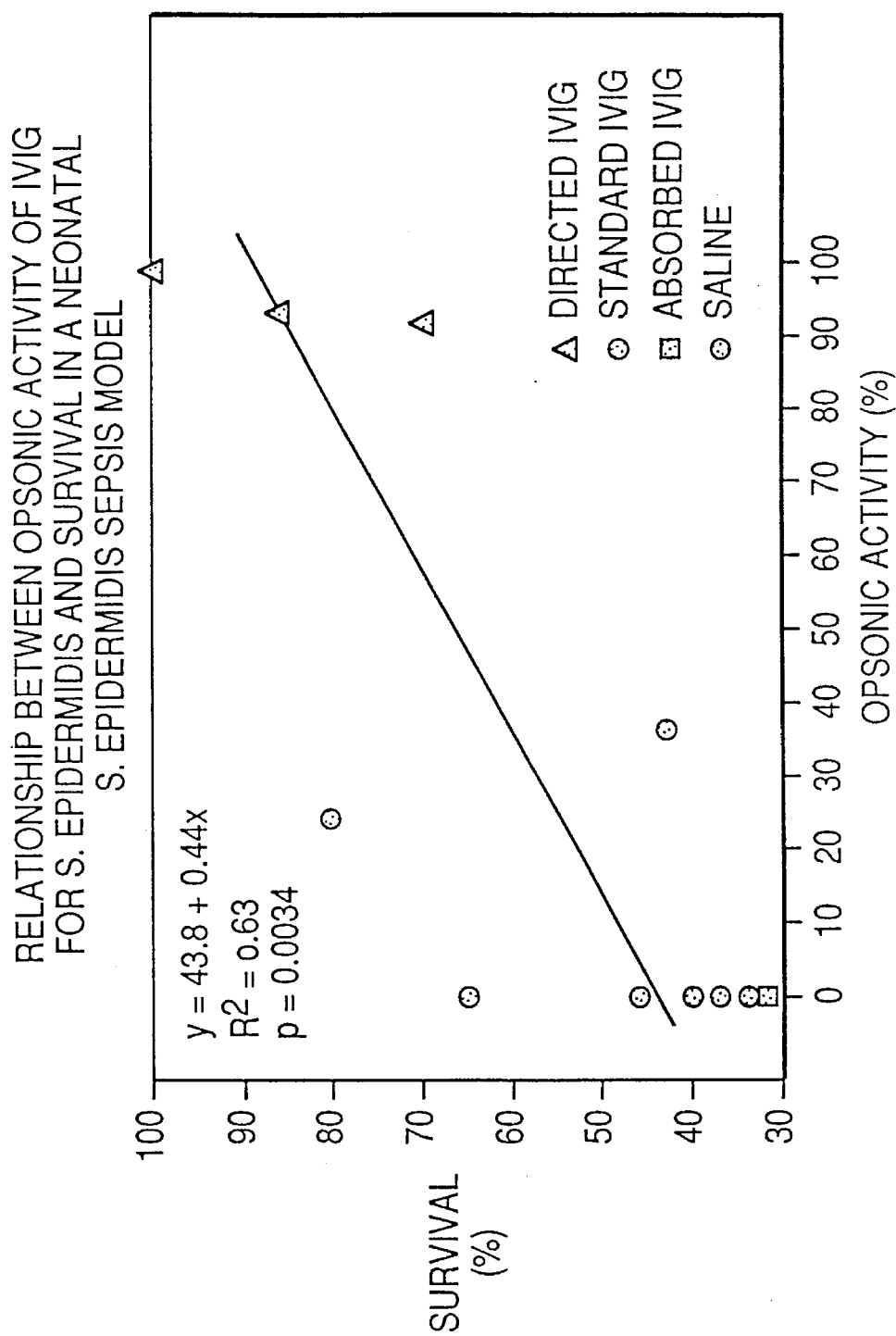

bodies, complement, and neutrophil function. Moreover, lipid infusion, which is now a standard ingredient of parenteral nutrition therapy, further impairs the already poor immune response of these infants to bacterial infection (G. W. Fischer et al., Lancet 2:819 (1980)).

BROADLY REACTIVE OPSONIC ANTIBODIES THAT REACT WITH COMMON STAPHYLOCOCCAL ANTIGENS

I. GOVERNMENT INTEREST

The invention described herein may be manufactured, licensed and used by or for governmental purposes without the payment of any royalties to us thereon.

II. CROSS REFERENCE TO RELATED APPLICATIONS

This application is a continuation of U.S. application Ser. No. 07/854,027, filed Mar. 19, 1992, now abandoned, which is a continuation-in-part of U.S. application Ser. No. 07/804, 317, filed Feb. 25, 1992, now abandoned which is a continuation of U.S. application Ser. No. 07/601,089, filed Oct. 22, 1990 now abandoned.

III. FIELD OF THE INVENTION

This invention relates to immunoglobulin (including polyclonal antibodies and monoclonal antibodies) and isolated antigen used to prevent, diagnose, or treat Staphylococcus infections. This invention also relates to an animal model used to determine the efficacy of pharmacological compositions against infectious agents including, but not limited to, Staphylococcus infections.

IV. BACKGROUND OF THE INVENTION

Over the last two decades, Staphylococcus infections have become important causes of human morbidity and mortality, particularly in hospitalized patients. Because of their prevalence on the skin and mucosal linings, Staphylococci are ideally situated to produce infections, both localized and systemic. Debilitated or immunosuppressed patients are at extreme risk of systemic infection.

The Staphylococcus species most frequently pathogenic in humans are *Staphylococcus aureus* and *Staphylococcus epidermidis*, and each includes a number of serotypes. Both groups have developed resistance to antibiotics, the current treatment of choice. In recent years, *S. epidermidis* has become a major cause of nosocomial infection in patients whose treatments include the placement of foreign objects such as cerebrospinal fluid shunts, cardiac valves, vascular catheters, joint prostheses, and other implants into the body. *S. epidermidis* is also a common cause of post-operative wound infections and peritonitis in patients with continuous ambulatory peritoneal dialysis. One form of treatment for kidney failure entails the introduction of large volumes of peritoneal dialysis fluid into the peritoneal cavity which carries the risk of frequent and recurrent infections. In a similar manner, patients with impaired immunity and those receiving parenteral nutrition through central venous catheters are at high risk for developing *S. epidermidis* sepsis as well (C. C. Patrick, J. Pediatr., 116:497 (1990)).

*S. epidermidis* has also become a common cause of neonatal nosocomial sepsis. Infections frequently occur in premature infants that have received parenteral nutrition which can be a direct or indirect source of contamination. Such infections are difficult to treat for a variety of reasons. Resistance to antibiotics is common. In one study, the majority of staphylococci isolated from blood cultures of septic infants were multiply resistant to antibiotics (A. Fleer et al., Pediatr. Infect. Dis. 2:426 (1983)). Stimulation of the immune system provides little relief because such infants have impaired immunity resulting from deficiencies in antibodies, complement, and neutrophil function. Moreover, lipid infusion, which is now a standard ingredient of parenteral nutrition therapy, further impairs the already poor immune response of these infants to bacterial infection (G. W. Fischer et al., Lancet 2:819 (1980)).

Supplemental immunoglobulin therapy has been shown to provide some measure of protection against certain encapsulated bacteria such as *Hemophilus influenzae* and *Streptococcus pneumoniae*. Infants who are deficient in antibody are susceptible to infections from these bacteria and bacteremia and sepsis are common. When anti-Streptococcal and anti-Hemophilus antibodies are present, they provide protection by promoting clearance of the respective bacteria from the blood. In the case of antibody to Staphylococcus, the potential use of supplemental immunoglobulin to prevent or treat infection has been much less clear.

Early studies of Staphylococcus infections focused on the potential use of supplemental immunoglobulin to boost peritoneal defenses, such as opsonic activity, in patients receiving continuous ambulatory peritoneal dialysis. Standard intravenous immunoglobulin (IVIG) was shown to have lot to lot variability for opsonic activity to *S. epidermidis* (L. A. Clark and C. S. F. Easmon, J. Clin. Pathol. 39:856 (1986)). In this study, one third of the IVIG lots tested had poor opsonization with complement, and only two of fourteen were opsonic without complement. Thus, despite the fact that the IVIG lots were made from large plasma donor pools, good opsonic antibody to *S. epidermidis* was not uniformly present. Moreover, this study did not examine whether IVIG could be used to prevent or treat *S. epidermidis* infections or bacterial sepsis.

Recent studies have associated coagulase-negative Staphylococcus bacteremia, such as *S. epidermidis*, as the most common species causing bacteremia in neonates receiving lipid emulsion infusion (J. Freeman et al., N. Engl. J. Med. 323:301 (1990)). These neonates had low levels of opsonic antibody to *S. epidermidis* despite the fact that the sera had clearly detectable levels of IgG antibodies to *S. epidermidis* peptidoglycan (A. Fleer et al., J. Infect. Dis. 2:426 (1985)). This was surprising because anti-peptidoglycan antibodies were presumed to be the principal opsonic antibodies. Thus, while suggesting that neonatal susceptibility to *S. epidermidis* might be related to impaired opsonic activity, these studies also suggested that many antibodies directed against *S. epidermidis* are not opsonic and would not be capable of providing protection when given passively to neonates.

Recently, an antigen binding assay was used to analyze IgG antibody to *S. epidermidis* in patients with uncomplicated bacteremia and those with bacteremia and endocarditis (F. Espersen et al., Arch. Intern. Med. 147:689 (1987)). This assay used an ultrasonic extract of *S. epidermidis* to identify *S. epidermidis* specific IgG. None of the patients with uncomplicated bacteremia had IgG antibodies to *S. epidermidis*. These data suggest that IgG does not provide effective eradication of *S. epidermidis* from the blood. In addition, 89% of bacteremic patients with endocarditis developed high levels of IgG to *S. epidermidis*. In these patients, IgG was not protective since high levels of IgG antibody were associated with serious bacteremia and endocarditis. Based on these studies, the protective role of IgG in *S. epidermidis* sepsis and endocarditis was questionable, especially in the presence of immaturity, debilitation, intralipid infusion, or immunosuppression.

Animal studies in the literature that demonstrated immunoglobulin protection against Staphylococcus infections have shown strain specificity by enzyme-linked immunosorbent assays (ELISA) and have utilized normal adult mice in protection studies. These studies do not mimic the disease as observed in humans. Animal models typically have used mature animals with normal immunity and then given unusually virulent strains or overwhelming-challenge doses of bacteria. Human patients are generally immunologically immature or debilitated. Human patients also get somewhat indolent infections with low virulence pathogens such as *S. epidermidis* with death usually attributable to secondary complications. Models that have used unusual strains or overwhelming bacterial doses, generally induce rapid fulminant death. These are important factors since antibodies generally work in concert with the host cellular immune system (neutrophils, monocytes, macrophages and fixed reticuloendothelial system). The effectiveness of antibody therapy may therefore be dependent on the functional immunologic capabilities of the host. To be predictive, animal models must closely emulate the clinical condition in which the infection would occur and capture the setting for therapy. Moreover, the animal studies have yielded inconsistent results.

One model has been reported which used an unusually virulent strain of *S. epidermidis*. Infected-mature mice developed 90 to 100% mortality within 24 to 48 hours (K. Yoshida et al., Japan. J. Microbiol. 20:209 (1976)). Antibody to *S. epidermidis* surface polysaccharide was protective in these mice. Protection was shown to occur with an IgM fraction, but not the IgG fraction (K. Yoshida and Y. Ichiman, J. Med. Microbiol. 11:371 (1977)). This model, however, presents a pathology which is very different from that seen in typically infected patients. Intraperitoneally-challenged mice developed symptoms of sepsis within minutes of receiving the injection and died in 24 to 48 hours. This particular pathology is not observed in Staphylococcus infected humans. The highly virulent strain of *S. epidermidis* may represent an atypical type of infection. Moreover, isolates of *S. epidermidis* from infected humans did not kill mice in this model.

In 1987, these animal studies were extended to include the evaluation of antibodies in human serum against selected virulent strains of *S. epidermidis* (Y. Ichiman et al., J. Appl. Bacteriol. 63:165 (1987)). In contrast to the previous data, protective antibody was found in the IgA, IgM and IgG immunoglobulin fractions. A definitive role for any single class of immunoglobulin (IgG, IgM, IgA) could not be established.

In this animal model, normal adult mice were used and mortality was determined. Death was considered to be related to the effect of specific bacterial toxins, not sepsis (K. Yoshida et al., Japan J. Microbiol. 20:209 (1976)). Most clinical isolates did not cause lethal infections, and quantitative blood cultures were not done. Moreover, this study provided little insight as to whether antibody could successfully prevent or treat *S. epidermidis* sepsis in immature or immunosuppressed patients.

In a later study, serotype specific antibodies directed against *S. epidermidis* capsular polysaccharides were tested in the animal model. Results showed that serotype-specific antibodies were protective, but that each antibody was directed against one serotype as measured by ELISA. Protection was equally serotype specific. Protection against heterologous strains did not occur. In addition, it was concluded that protection was afforded by the IgM antibody.

In short, there has been no compelling evidence that IVIG would be effective to treat *S. epidermidis* infections or sepsis, particularly where the patients are immature or immune suppressed or where multiple *S. epidermidis* serotypes are involved. Thus, for example, a recent and extensive review of the pathogenesis, diagnosis, and treatment of *S. epidermidis* infections does not include immunoglobulin as a potential prophylactic or therapeutic agent (C. C. Patrick, J. Pediatr. 116:497 (1990)).

In addition, no animal model has been developed which is comparable to human patients with *S. epidermidis* infections, particularly those who are immature or immune suppressed. This is critical because these patients have low levels of complement as well as impaired neutrophil and macrophage function. Thus, even if opsonic activity of immunoglobulin may appear adequate under optimal conditions in vitro, protection may not occur in patients such as newborn babies or cancer patients. Moreover, previous models have been shown to be unsatisfactory in that they used animals which did not possess similar risk factors to the typical high-risk human patient.

At present, antibiotic therapy is the treatment of choice for the prevention and cure of Staphylococcus infections in humans. Although new antibiotics are constantly being developed, it has become increasing clear that antibiotic therapy alone is insufficient. The data regarding passive vaccinations with immunoglobulin is at best unclear. The animal models on which this therapy has been attempted bear little relationship to human infections and as yet, have produced no definitive solutions.

V. SUMMARY OF THE INVENTION

The present invention overcomes the problems and disadvantages associated with current strategies and designs and provides a new therapy for the treatment and prevention of Staphylococcus infections. As broadly described herein, this invention relates to the discovery that there are broadly reactive opsonic antibodies that react with common staphylococcal antigens from which vaccines, pharmaceutical compositions, and diagnostic aids can be created for the treatment and prevention of Staphylococcus infections in both man and animals. The invention includes immunoglobulin, which may be found in individual samples or pools of serum, plasma, whole blood, or tissue, isolated immunoglobulin, which may be polyclonal antibodies or monoclonal antibodies, methods for making polyclonal and monoclonal antibodies, isolated antigen, methods for making isolated antigen, pharmaceutical compositions comprising isolated immunoglobulin or isolated antigen, and methods for the prophylactic or therapeutic treatment of a patient with the pharmaceutical compositions. In addition, this invention also comprises an animal model to evaluate the efficacy of pharmaceutical compositions in vivo, diagnostic aids and methods for the detection of a Staphylococcus infection, and methods to detect pharmaceutical compositions in biological samples, including pharmaceutical compositions as described herein.

In accord with this invention, and as broadly described herein, a first object of the present invention is the identification of immunoglobulin, which may be from individual samples or pools of serum, plasma, whole blood, or tissue for the treatment of a Staphylococcus infection. Immunoglobulin is identified by performing a first assay to identify immunoglobulin which is reactive with a preparation of a first Staphylococcus organism, performing a second assay to identify immunoglobulin which is reactive with a preparation of a second Staphylococcus organism, and selecting immunoglobulin which is reactive with the preparations from both the first and second Staphylococcus organisms. Reactivity is determined in immunological assays which may be binding assays, opsonization assays, or clearance assays. Preferably, the preparations of the first and the second Staphylococcus organisms are derived from different serotypes or different species, such as *S. epidermidis* and *S. aureus*, and more preferably, the first preparation is from *S. epidermidis* (Hay, ATCC 55133).

In accord with this invention, and as broadly described herein, a second object of the present invention is the isolation of immunoglobulin which reacts in a first assay with a preparation of a first Staphylococcus organism and in a second assay with a preparation of a second Staphylococcus organism. The invention includes the isolation of polyclonal antibodies, which are produced by introducing a preparation of a Staphylococcus organism into an animal and isolating serum, and monoclonal antibodies, which are produced by hybridoma technology. Preferably, the isolated immunoglobulin is of the IgG fraction or isotype, but isolated immunoglobulin is not restricted to any particular fraction or isotype and may be IgG, IgM, IgA, IgD, IgE, or any combination thereof. It is also preferable that the isolated immunoglobulin be purely or antigenically human immunoglobulin, which may be made directly by the fusion of human antibody producing cells with human antibody producing cells or by the substitution of human DNA sequences for some of the nonhuman DNA sequences which code for the antibody while retaining the antigen binding ability of the original antibody molecule. Isolated immunoglobulin may be used to treat patients infected with or suspected of being infected with a Staphylococcus organism, and prophylactically to prevent possible Staphylococcus infections. Further, isolated immunoglobulin may be used prophylactically to treat objects, articles, instruments and appliances which are introduced into a patient and are suspected of becoming infected with and introducing a Staphylococcus infection into a patient.

In accord with this invention, and as broadly described herein, a third object of the present invention is isolated antigen which generates an antibody that reacts in a first assay with a preparation of a first Staphylococcus organism and in a second assay with a preparation of a second Staphylococcus organism. As used herein, isolated antigen means any single antigen, any mixture of different antigens, or any combination of antigens which are separated from one or more different Staphylococcus organisms. Isolated antigen may be used directly as a pharmaceutical composition, such as a Staphylococcus vaccine, and indirectly to generate antibodies, both monoclonal and polyclonal, to treat or prevent Staphylococcus infections in man and animals.

In accord with this invention, and as broadly described herein, a fourth object of the present invention is the identification of an animal model to evaluate the efficacy of pharmaceutical compositions in vivo. This animal model may be broadly applied to test the efficacy of a wide variety of pharmaceuticals against infection by bacteria, preferably Staphylococci, but also viruses, parasites and fungi. It comprises the administration of a pharmaceutical composition, an immune suppressant, and an infectious agent to an immature animal, and evaluating whether the pharmaceutical composition reduces mortality of the animal or enhances clearance of the infectious agent from the animal. The pharmaceutical composition may be isolated immunoglobulin or isolated antigen of the invention as described herein, and may be administered prophylactically or therapeutically.

In accord with this invention, and as broadly described herein, a fifth object of the present invention comprises diagnostic aids and methods for the diagnosis of Staphylococcus infections which employ as reagents isolated immunoglobulin, isolated antigen or preparations of Staphylococcus organisms. These reagents are also of use to detect pharmaceutical compositions in biological samples to analyze the utility of a particular pharmaceutical composition, including pharmaceutical compositions described herein. In addition, these reagents are also highly useful as tools to examine the biology of the Staphylococcus organism and its course of infection experimentally in a laboratory setting.

Other objects and advantages of the present invention will be set forth in part in the description which follows, and in part will be obvious from this description, or may be learned from the practice of this invention. The accompanying drawings and tables, which are incorporated in and constitute a part of this specification, illustrate and, together with this description, serve to explain the principle of the invention.

VI. BRIEF DESCRIPTIONS OF THE DRAWINGS

FIG. 1. Antibody titers of human plasma tested for binding to *S. epidermidis* serotypes I, II, III, and Hay.

Figure 2:
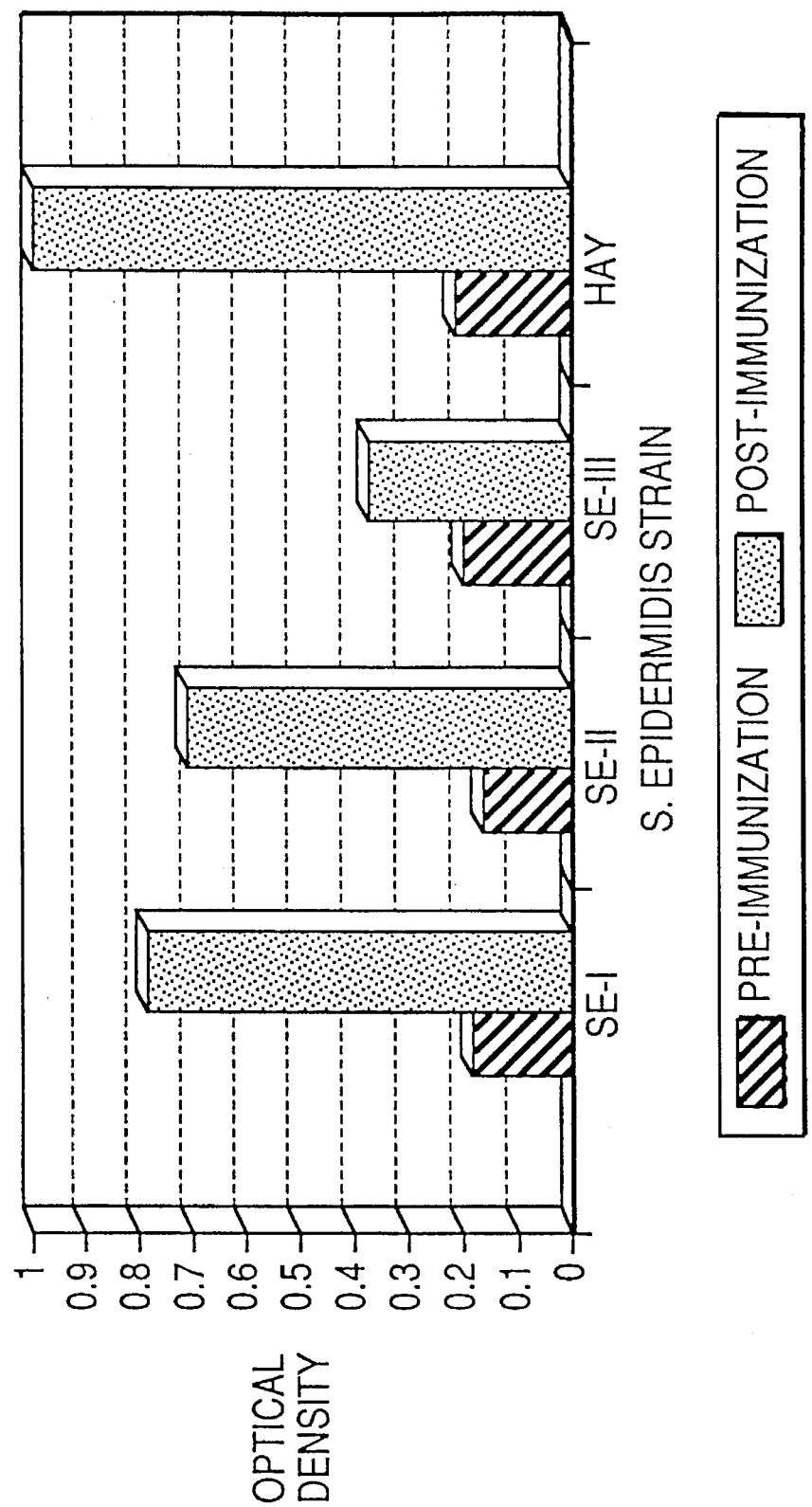

FIG. 2. Pre- and post-immunization ELISA titers of sera from rabbits immunized with a TCA prepared preparation of *S. epidermidis* (Hay, ATCC 55133) tested for binding to *S. epidermidis* serotypes I, II, III and Hay.

Figure 3:
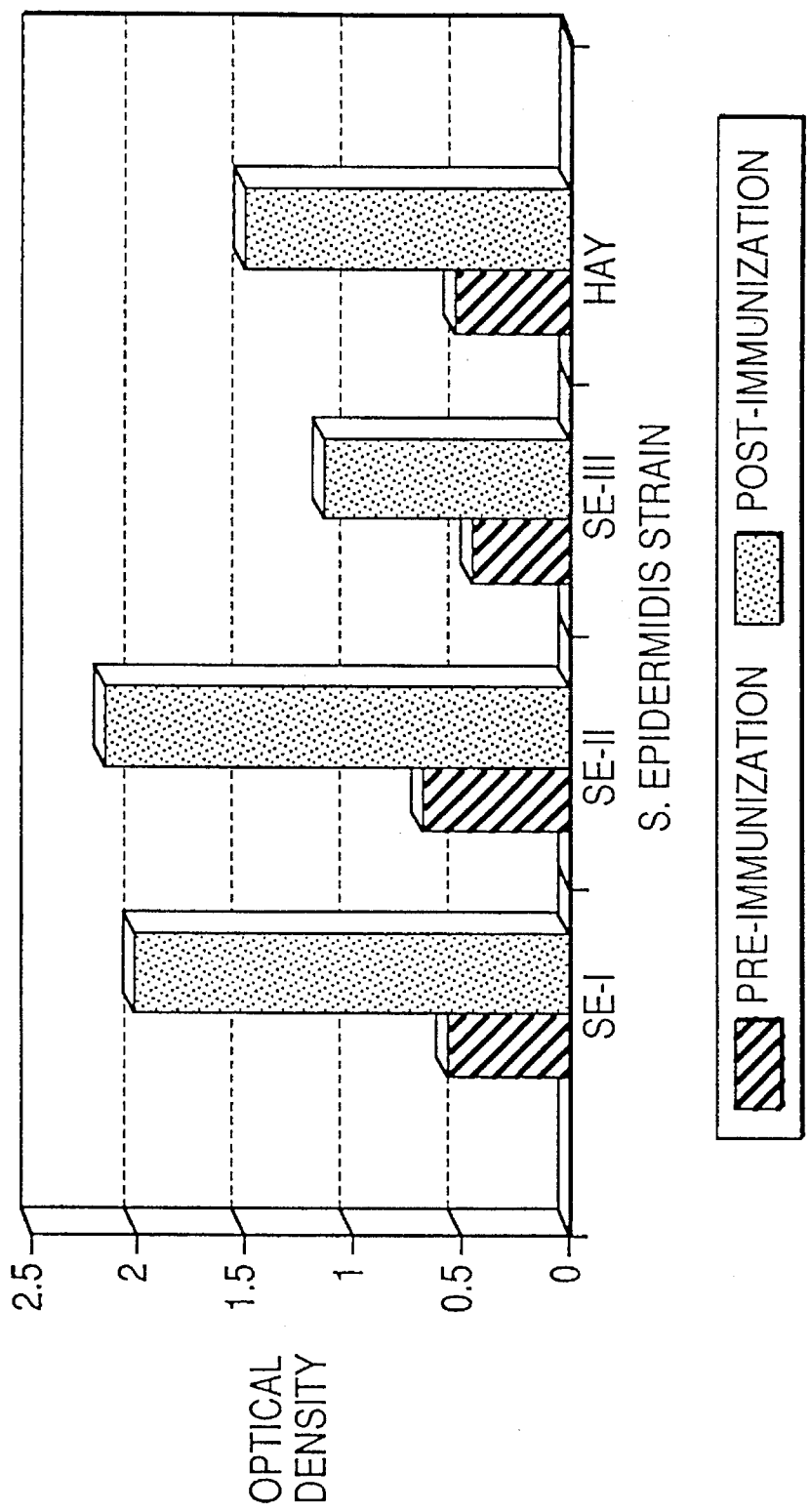

FIG. 3. Pre- and post-immunization ELISA titers of sera from rabbits immunized with a whole cell preparation of *S. epidermidis* (Hay, ATCC 55133) tested for binding to *S. epidermidis* serotypes I, II, III and Hay.

Figure 4:
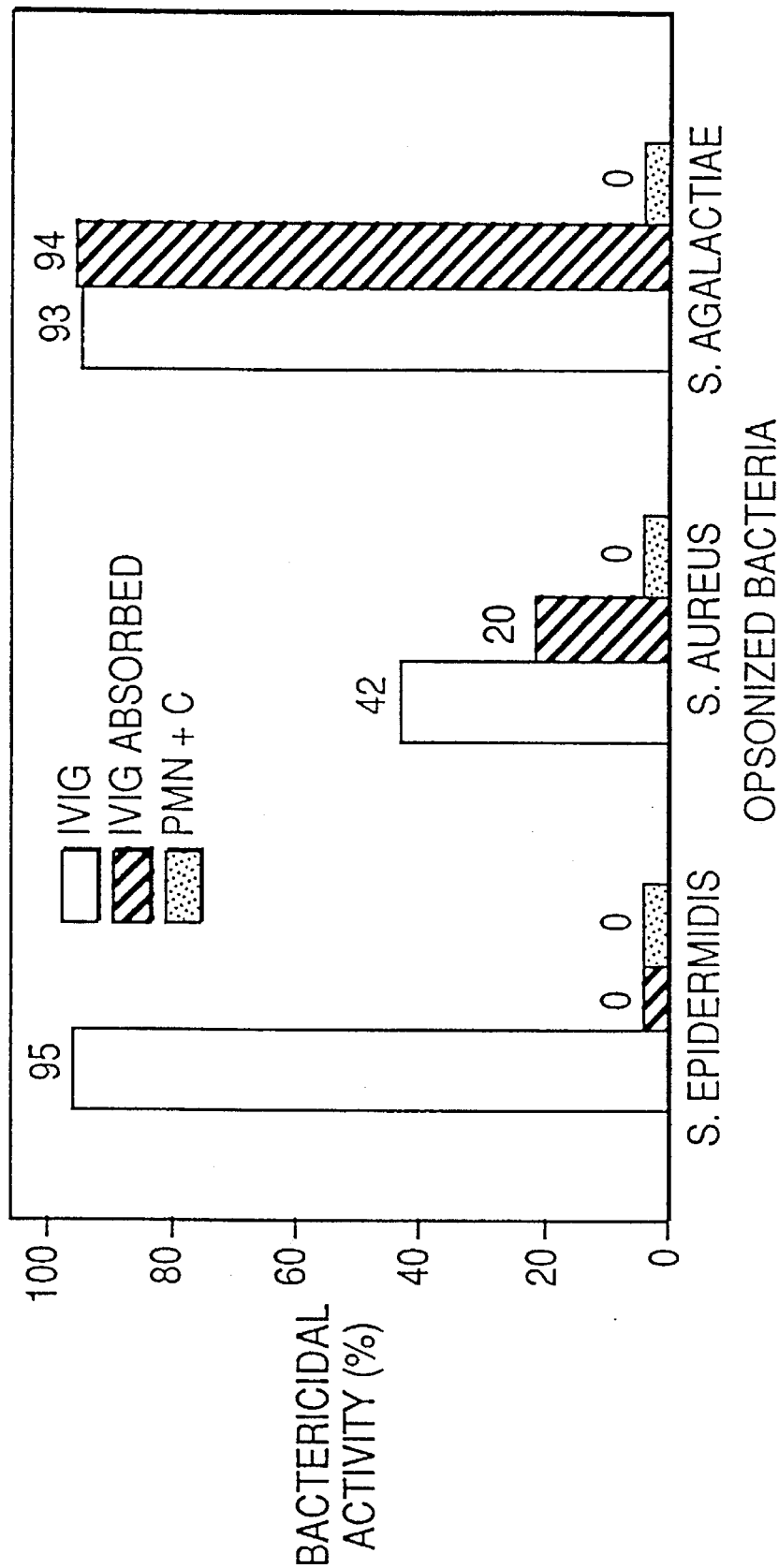

FIG. 4. Neutrophil mediated opsonization assay of *S. epidermidis*, *S. aureus*, and *Streptococcus agalactiae* organisms using immunoglobulin which has been selected for the ability to bind to a preparation of *S. epidermidis*, and selected immunoglobulin which has been preabsorbed with a preparation of *S. epidermidis*. Negative control is neutrophils plus complement alone.

Figure 5:
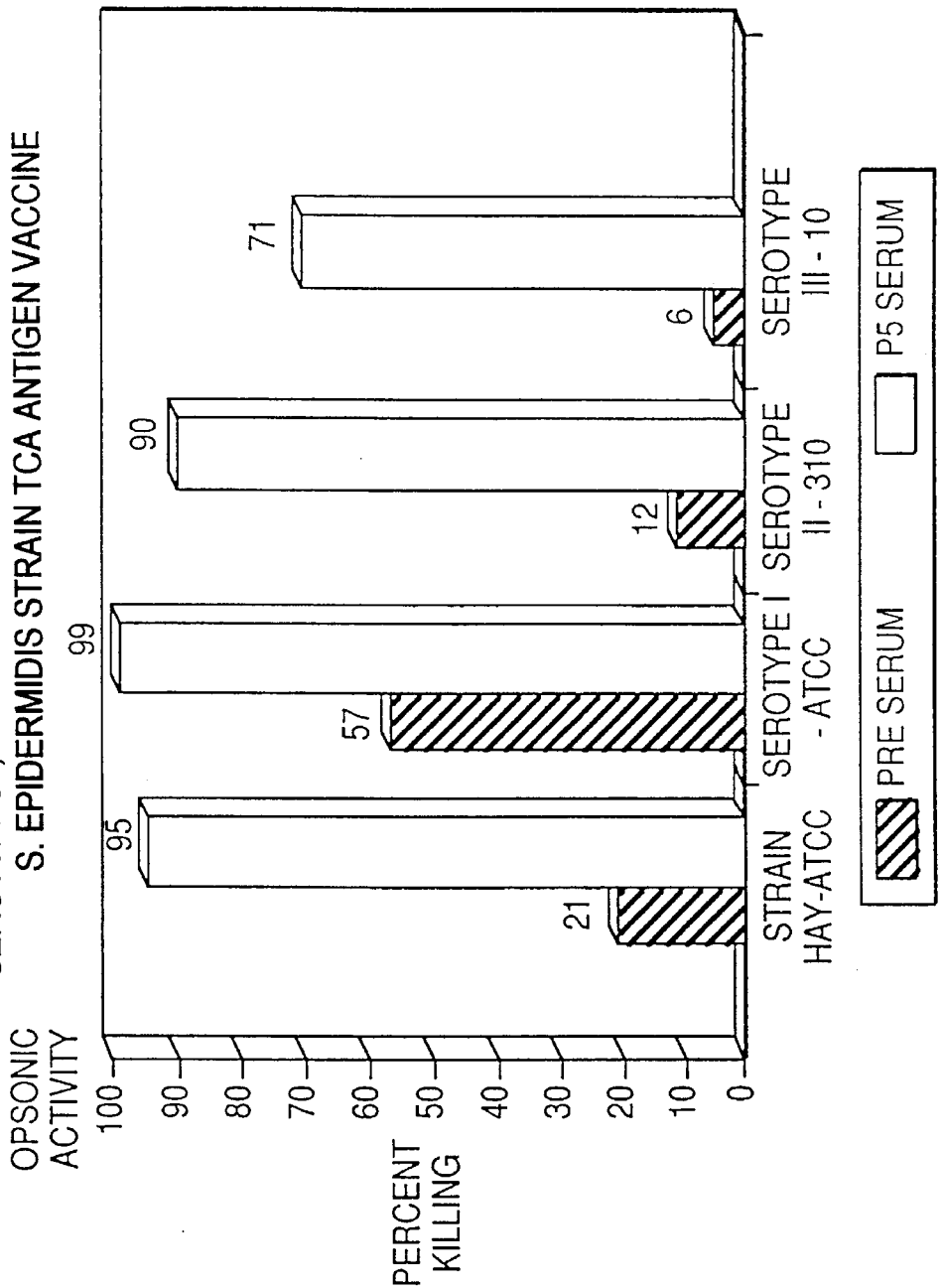

FIG. 5. Opsonic activity measured as percent bactericidal response of rabbit serum pre- and post-immunization with a TCA prepared preparation of *S. epidermidis* (Hay, ATCC 55133) against *S. epidermidis* serotypes I, II, III, and Hay.

Figure 6:
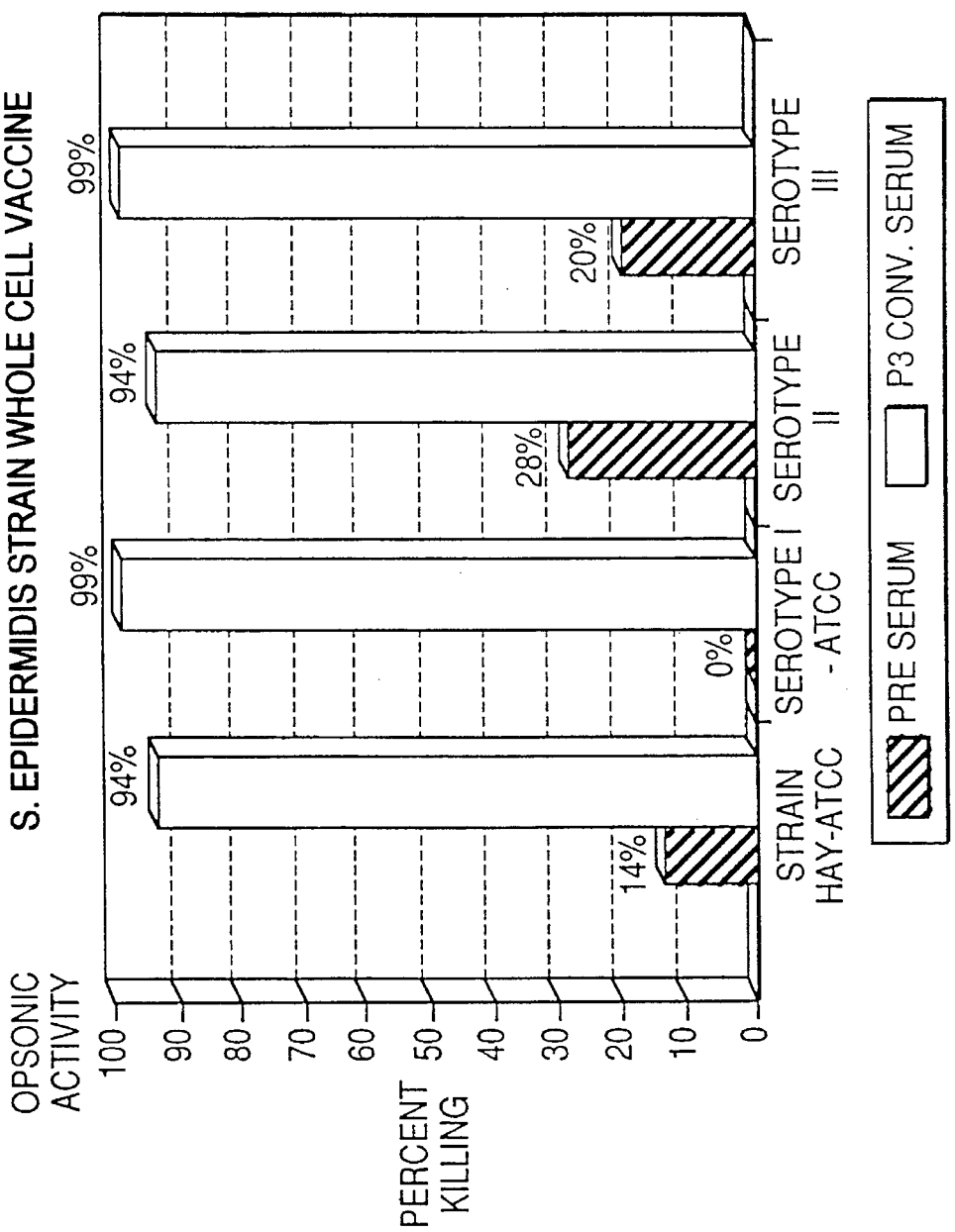

FIG. 6. Opsonic activity measured as percent bactericidal response of rabbit serum pre- and post-immunization with a whole cell preparation of *S. epidermidis* (Hay, ATCC 55133) against *S. epidermidis* serotypes I, II, III, and Hay.

Figure 7:
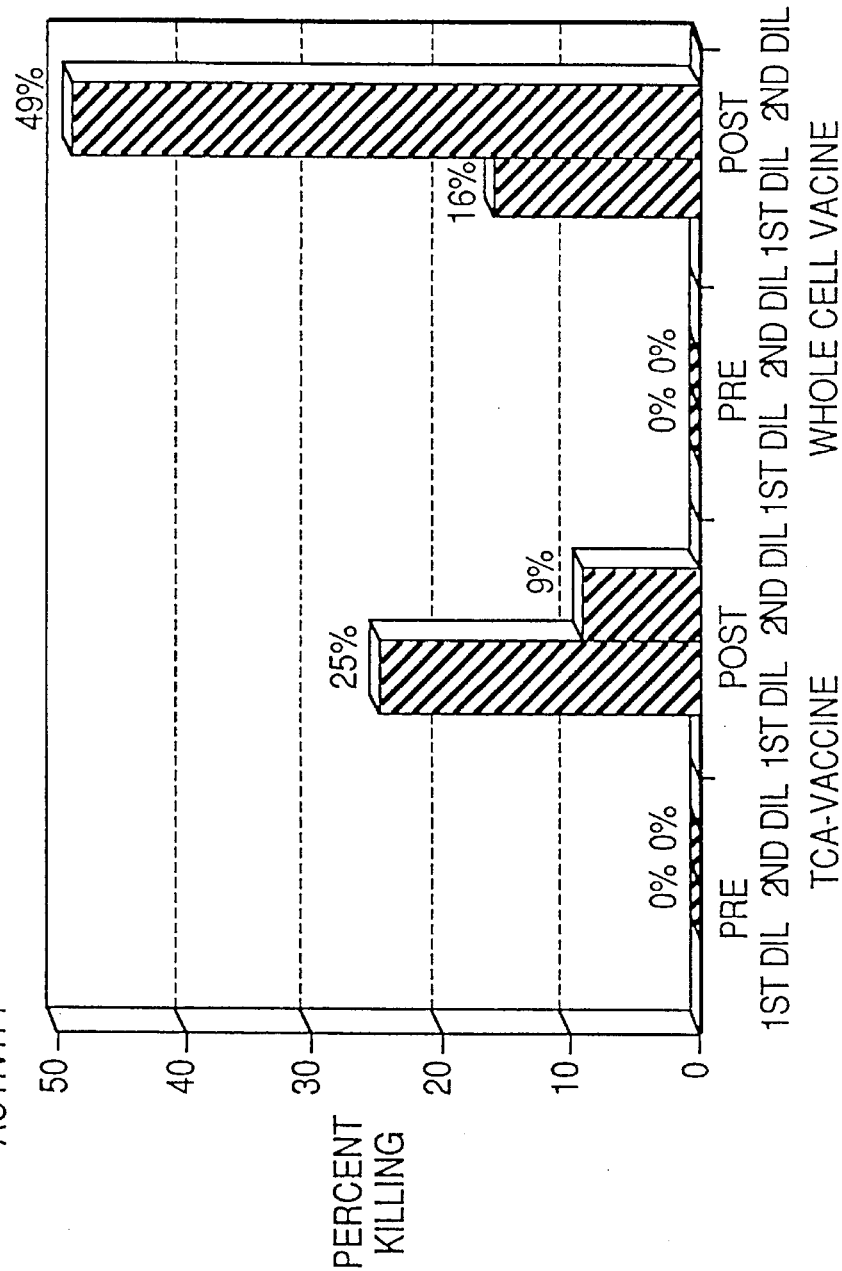

FIG. 7. Opsonic activity of pre- and post-immunization serum with TCA prepared or whole cell preparation of *S. epidermidis* (Hay, ATCC 55133) against *S. aureus* type 5. Opsonic assays were calculated using two dilutions of the reaction mixture prior to subculturing onto solid agar.

Figure 8:
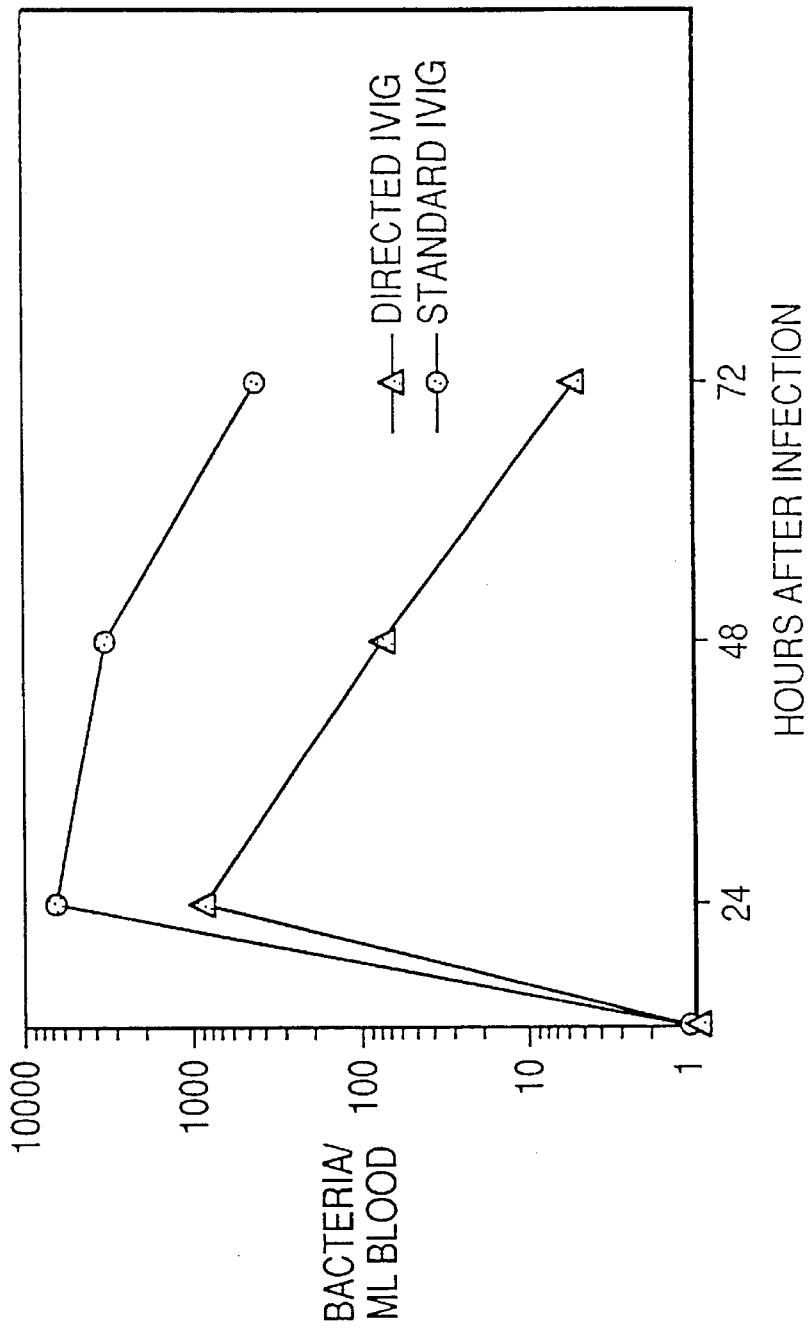

FIG. 8. Bacteremia levels of *S. epidermidis* in samples of blood from suckling rats treated with either high-titer immunoglobulin, selected for the ability to bind to a preparation of *S. epidermidis*, or unselected low-titer immunoglobulin.

Figure 9:
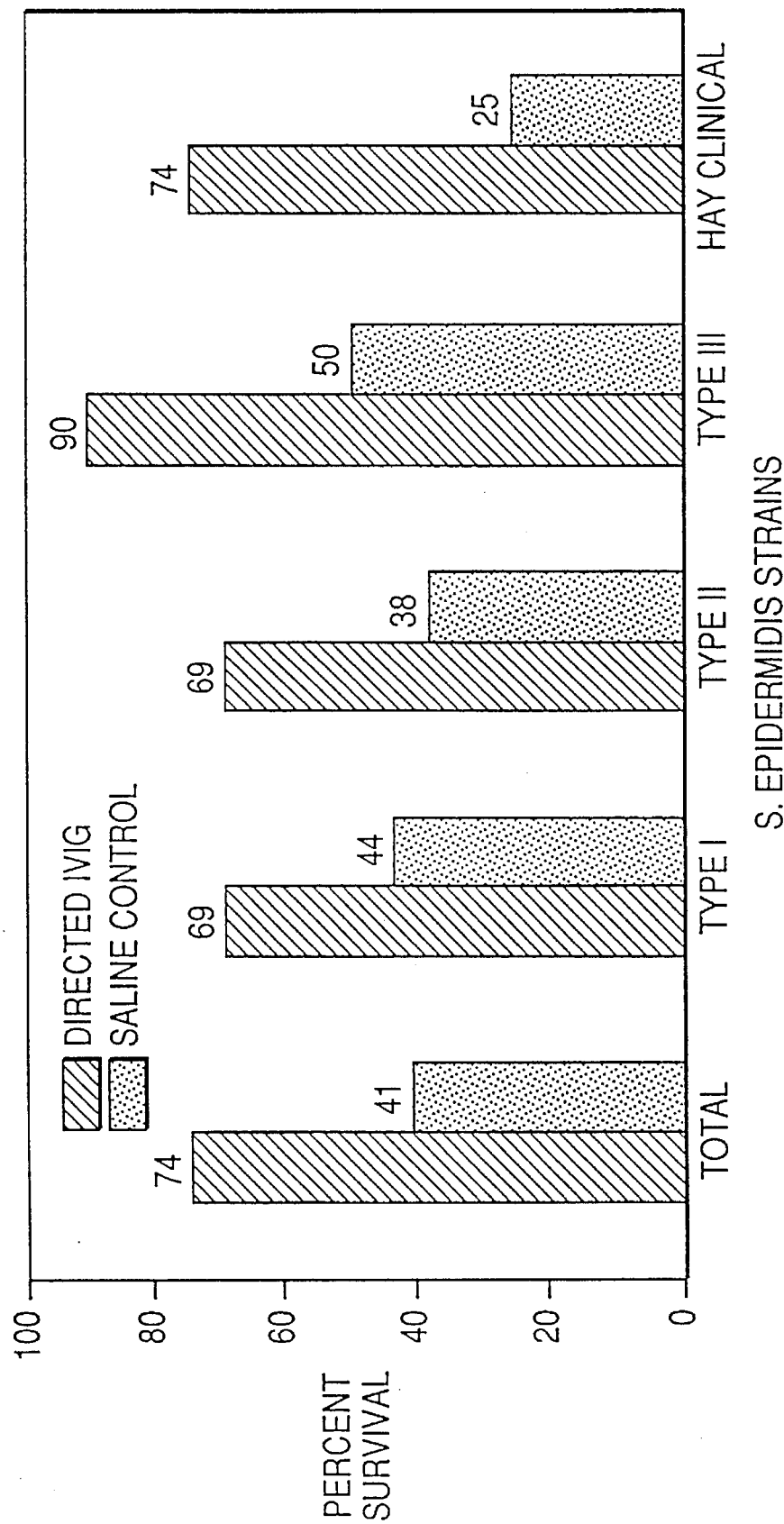

FIG. 9. Effect of directed (selected high-titer) immunoglobulin and saline injections on survival in suckling rats treated with intralipid plus *S. epidermidis*.

Figure 10:
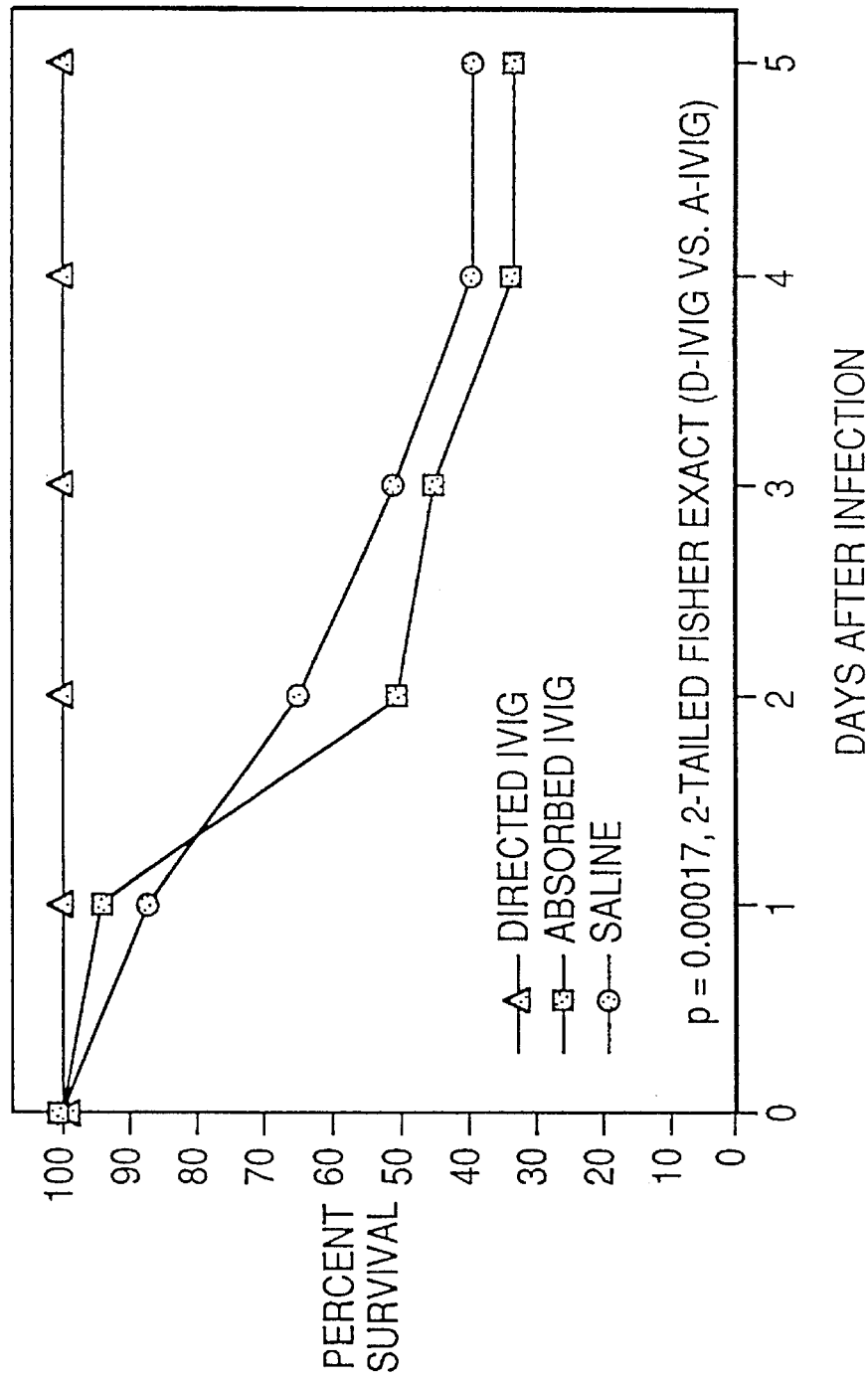

FIG. 10. Effect of directed (selected high-titer) immunoglobulin, directed immunoglobulin preabsorbed with a preparation of *S. epidermidis*, and saline injections on survival in suckling rats treated with intralipid plus *S. epidermidis*.

Figure 11:
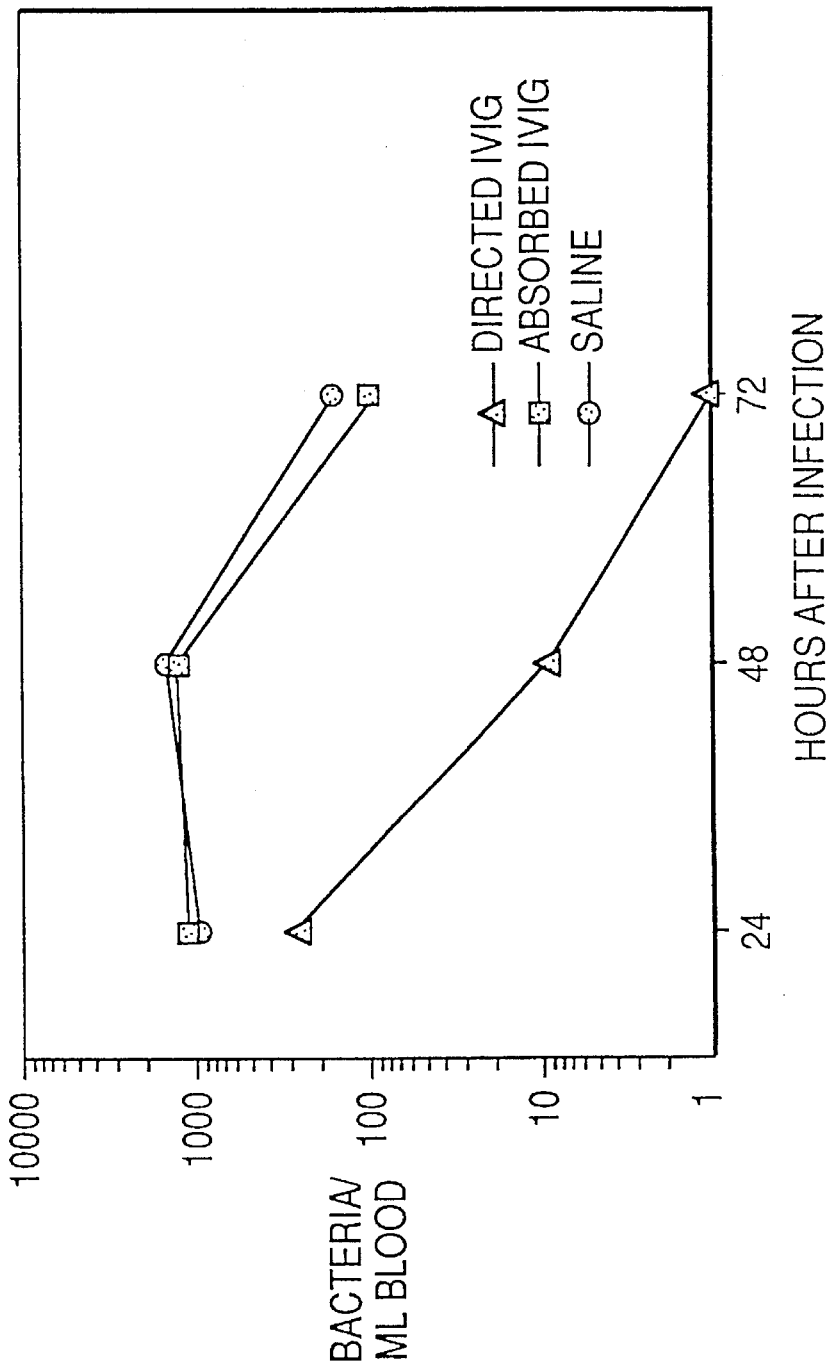

FIG. 11. Effect of directed (selected high-titer) immunoglobulin, directed immunoglobulin preabsorbed with a preparation of *S. epidermidis,* and saline injections on bacteremia levels in the blood of suckling rats treated with intralipid plus *S. epidermidis.*

FIG. 12. Relationship between opsonic activity measured in vitro and survival in the suckling rat model with directed (selected high-titer) immunoglobulin, unselected low-titer immunoglobulin, directed immunoglobulin which has been preabsorbed with a preparation of *S. epidermidis,* and saline.

VII. DESCRIPTION OF PREFERRED EMBODIMENTS

To achieve the objects and in accordance with the purpose of the invention, as embodied and broadly described herein, the present invention comprises the identification, making, and isolation of immunoglobulin and antigen useful to prevent, diagnose, or treat Staphylococcus infections. The invention further comprises an in vivo animal model for testing the efficacy of pharmaceutical compositions, including compositions of immunoglobulin and preparations described herein.

One embodiment of the present invention is a method of identifying immunoglobulin for the treatment of a Staphylococcus infection, comprising the steps of performing a first assay to identify immunoglobulin which is reactive with a preparation of a first Staphylococcus organism, performing a second assay to identify immunoglobulin which is reactive with a preparation of a second Staphylococcus organism, and selecting immunoglobulin which is reactive with the preparations from both the first and second Staphylococcus organisms. The immunoglobulin may be derived from pooled or individual samples of plasma, serum, whole blood, or tissue such as placenta. Although the isolation of immunoglobulin is not required, if it is determined to be necessary, such procedures are well-known to those of ordinary skill in the art. The first and second assays may be any immunological assays and preferably are binding assays, opsonization assays, clearance assays, or any combination of these assays. Preferably, the first and second Staphylococcus organisms are of different serotypes or of different species.

The first and second preparations of a Staphylococcus organism may be any preparations of a Staphylococcus organism including intact cells, cells fractionated by chemical or physical means, or cell extracts and is preferably a whole-cell or cell surface extract. It is preferred that one preparation is from *S. epidermidis* (Hay, ATCC 55133). A preparation of a Staphylococcus organism is comprised of polysaccharides, proteins, lipids and other bacterial cell components. It is preferred that the preparation is a polysaccharide and protein preparation, i.e., a preparation that predominantly contains mixtures or combinations of polysaccharides, proteins and glycoproteins. A suitable preparation may be prepared by isolating a culture of bacterial cells of *Staphylococcus epidermidis* (Hay, ATCC 55133), suspending the isolated cells in a mixture comprised of a solution of trichloroacetic acid, stirring the mixture at approximately 4° C., centrifuging the mixture and saving the resulting supernatant, combining the supernatant with an alcohol, preferably absolute ethanol, incubating the alcohol-supernatant combination at approximately 4° C. to precipitate a preparation, and isolating the precipitated preparation.

One preferred assay is a binding assay wherein immunoglobulin is reacted with a preparation of a Staphylococcus organism. The binding assay is preferably an enzyme-linked immunosorbent assay (ELISA), or a radio immune assay (RIA), but may also be an agglutination assay, a coagglutination assay, a colorimetric assay, a fluorescent binding assay, or any other suitable binding assay. It may be performed by competitive or noncompetitive procedures with results determined directly or indirectly.

In the binding assay, the preparation of a Staphylococcus organism may be fixed to a solid support which may be any surface suitable for supporting the preparation. Preferably, the solid support is a glass or plastic plate, well, bead, micro-bead, paddle, propeller, or stick, and is most preferably a titration plate. The fixed preparation is incubated with immunoglobulin, which may be isolated or within a biological fluid, and the amount of binding determined. A positive reaction occurs when the amount of binding observed is greater than the amount of binding of a negative control. A negative control is any sample which is known not to contain antigen specific immunoglobulin. Positive binding may be determined from a simple positive/negative reaction or from the calculation of a series of reactions. This series may include samples which contain measured amounts of immunoglobulin that specifically bind to the fixed antigen creating a standard curve from which the amount of antigen specific immunoglobulin in an unknown sample can be determined. Alternatively, the assay may be performed in substantially the same way with antibody fixed to the solid support and immunoglobulin identified by its ability to be retained to a preparation bound to the fixed antibodies.

Another preferred assay is an opsonization assay which may be a colorimetric assay, a chemilumenescent assay, a fluorescent or radiolabel uptake assay, a cell mediated bactericidal assay, or any other appropriate assay which measures the opsonic potential of a substance. In an opsonization assay, an infectious agent, a eukaryotic cell, and the to be tested opsonizing substance or an opsonizing substance plus a purported opsonizing enhancing substance, are incubated together. Most preferably, the opsonization assay is a cell mediated bactericidal assay. In this in vitro assay an infectious agent, typically a bacterium, a phagocytic cell and an opsonizing substance, in this case immunoglobulin, are incubated together. Although any eukaryotic cell with phagocytic or binding ability may be used in a cell mediated bactericidal assay, a macrophage, a monocyte, a neutrophil or any combination of these cells is preferred. Complement proteins may be included to observe opsonization by both the classical and alternate pathways.

The opsonic ability of immunoglobulin is determined from the amount or number of infectious agents that remain after incubation. In a cell mediated bactericidal assay, this is accomplished by comparing the number of surviving bacteria between two similar assays, only one of which contains the purported opsonizing immunoglobulin or by measuring the numbers of viable organisms before and after incubation. A reduced number of bacteria after incubation in the presence of immunoglobulin indicates a positive opsonizing ability. In the cell mediated bactericidal assay, positive opsonization is determined by culturing the incubation mixture under appropriate bacterial growth conditions. Any significant reduction in the number of viable bacteria comparing pre- and post-incubation samples or between samples which contain immunoglobulin and those that do not is a positive reaction.

Another preferred method of identifying immunoglobulin for the treatment of a Staphylococcus infection employs a clearance assay. Preferably, the clearance assay is conducted in an animal model. A particularly useful animal model comprises the steps of administering a pharmaceutical composition, an immune suppressant, and a Staphylococcus organism to an immature animal, and evaluating whether the pharmaceutical composition reduces mortality of the animal or enhances clearance of the Staphylococcus organism from the animal. This assay may use any immature animal including the rabbit, the guinea pig, the mouse, the rat, or any other suitable laboratory animal. The suckling rat is most preferred. An immune suppressant is any substance which will impair the immune system of the animal to which it is administered and is selected from the group consisting of steroids, anti-inflammatory agents, prostaglandins, cellular immune suppressants, iron, silica, particles, beads, lipid emulsions and any other effective immune suppressant. Preferably, the immune suppressant is cyclosporin, dexamethasone, triamcinolone, cortisone, prednisone, ibuprofen or any other related compound or combination of compounds. More preferably the immune suppressant is a lipid emulsion, and the lipid emulsion of choice is intralipid. When the pharmaceutical composition is immunoglobulin, the assay measures the clearance potential of the administered immunoglobulin.

Clearance is evaluated by determining whether the pharmaceutical composition enhances clearance of the infectious agent from the animal. This is typically determined from a sample of biological fluid, such as blood, peritoneal fluid, or cerebrospinal fluid. The infectious agent is cultured from the biological fluid in a manner suitable for growth or identification of the surviving infectious agent. From samples of fluid taken over a period of time after treatment, one skilled in the art can determine the effect of the pharmaceutical composition on the ability of the animal to clear the infectious agent. However, further data may be obtained by measuring survival of animals administered the pharmaceutical composition over a period of time, preferably a period of days. Typically, both sets of data are utilized. Results are considered positive if the pharmaceutical composition enhances clearance or decreases mortality. In situations in which there is enhanced organism clearance, but the test animals still perish, a positive result is still indicated.

Another embodiment of the present invention is isolated immunoglobulin which is reactive in a first assay with a preparation of a first Staphylococcus organism, and in a second assay with a preparation of a second Staphylococcus organism. The first and second assays may be any immunological assays and preferably are binding assays, opsonization assays, clearance assays, or any combination of these assays. The first and second Staphylococcus organisms may be of different species, and are preferably *S. epidermidis* and *S. aureus*. Alternatively, the first and second Staphylococcus organisms may be of different serotypes, which are preferably *S. epidermidis* type I and *S. epidermidis* type II. In either case, it is most preferred, that one of the preparations of Staphylococcus organisms be *Staphylococcus epidermidis* (Hay, ATCC 55133). The first and second preparations of a Staphylococcus organism may be any preparations of a Staphylococcus organism including intact cells, cells fractionated by chemical or physical means, or cell extracts and is preferably a whole-cell or cell surface extract. It is preferred that one preparation is from *S. epidermidis* (Hay, ATCC 55133). A preparation of a Staphylococcus organism is comprised of polysaccharides, proteins, lipids and other bacterial cell components. It is preferred that the preparation is a polysaccharide and protein preparation, i.e., a preparation that predominantly contains mixtures or combinations of polysaccharides, proteins and glycoproteins. A suitable preparation may be prepared by isolating a culture of bacterial cells of *Staphylococcus epidermidis* (Hay, ATCC 55133), suspending the isolated cells in a mixture comprised of a solution of trichloroacetic acid, stirring the mixture at approximately 4° C. centrifuging the mixture and saving the resulting supernatant, combining the supernatant with an alcohol, preferably absolute ethanol, incubating the alcohol-supernatant combination at approximately 4° C. to precipitate a preparation, and isolating the precipitated preparation.

Isolated immunoglobulin of the present invention may be isolated from pooled or single units of blood, plasma, sera or tissue, such as placenta, or from any immunoglobulin preparation derived therefrom, such as intravenous immunoglobulin (IVIG). Procedures for the isolation of immunoglobulin from these substances are well-known to those of ordinary skill in the art. Briefly, one method comprises the steps of removal of all cells and cellular debris from the fluid, and fractionation of the immunoglobulin portion of the fluid by methods such as chromatography, precipitation, or extraction. Details of these procedures and others are described in *Protein purification: Principles and Practice* (R. K. Scopes, Springer-Verlag, New York, 1987), which is hereby specifically incorporated by reference by way of example.

Isolated immunoglobulin may be one or more antibodies of any isotype, including IgG, IgM, IgD, IgA, or IgE. Isolated immunoglobulin includes polyclonal antibodies, most preferably of the IgG fraction. Isolated immunoglobulin also includes monoclonal antibodies, most preferably of the IgG isotype. Procedures for the identification and isolation of a particular fraction or isotype of antibody are well-known in the subject art. Numerous methods, by way of example, are disclosed in *Current Protocols in Immunology* (J. E. Coligan et al., eds., John Wiley & Sons, New York, 1991), which is hereby specifically incorporated by reference. The present invention also includes methods for making these antibodies.

A method for making polyclonal antibodies for the treatment of a Staphylococcus infection comprises the steps of introducing a preparation of a Staphylococcus organism to a mammal, removing serum from the meal, and isolating polyclonal antibodies which react in a first assay with a preparation of a first Staphylococcus organism and in a second assay with a preparation of a second Staphylococcus organism. The first and second assays may be any immunological assays and preferably are binding assays, opsonization assays, clearance assays, or any combination of these assays. The first and second preparations of a Staphylococcus organism may be any preparations of a Staphylococcus organism including intact cells, cells fractionated by chemical or physical means, or cell extracts and is preferably a whole-cell or cell surface extract. The preparation of a Staphylococcus organism introduced into a mammal may also be any preparation of a Staphylococcus organism including intact cells, cells fractionated by chemical or physical means, or cell extracts and is preferably a whole-cell or cell surface extract. It is preferred that the preparation is from *S. epidermidis* (Hay, ATCC 55133). A preparation of a Staphylococcus organism is comprised of polysaccharides, proteins, lipids and other bacterial cell components. It is preferred that the preparation is a polysaccharide and protein preparation, i.e., a preparation that predominantly contains mixtures or combinations of polysaccharides, proteins and glycoproteins. A suitable preparation may be prepared by isolating a culture of bacterial cells of *Staphylococcus epidermidis* (Hay, ATCC 55133), suspending the isolated cells in a mixture comprised of a solution of trichloroacetic acid, stirring the mixture at approximately 4° C., centrifuging the mixture and saving the resulting supernatant, combining the supernatant with an alcohol, preferably absolute ethanol, incubating the alcohol-supernatant combination at approximately 4° C. to precipitate a preparation, and isolating the precipitated preparation.

The Staphylococcus preparation introduced into a mammal and used to make polyclonal antibodies may include specific and nonspecific adjuvants. Nonspecific adjuvants are substances which non-specifically stimulate the immune response to an antigen and includes Freunds, water-oil emulsions, surfactants, mineral oils, synthetic polymers, aluminum hydroxide, acrylamide, and other suitable response enhancing substances. Specific adjuvants include specific T and B cell stimulators which enhance the production of antibody by antibody producing cells.

A method for making monoclonal antibodies for the treatment of a Staphylococcus infection comprises creation of hybridoma cells which produce monoclonal antibodies. Such procedures are well-known in the art. Certain methods, by way of example, are specifically described in *Antibodies: A Laboratory Manual* (E. Harlow and D. Lane, Cold Spring Harbor Lab., 1988), which is hereby incorporated by reference. One method comprises the isolation of antibody producing cells, fusing the antibody producing cells with myeloma cells to form hybridoma cells, and screening the resulting hybridoma cells for a cell that produces the claimed monoclonal antibody. The antibody producing cells isolated are selected from the group consisting of cells which have been sensitized by infection of a Staphylococcus organism in vivo, i.e., an infection, cells which have been sensitized by exposure to a preparation of a Staphylococcus organism as herein described, in vivo, i.e., an immunization, cells which have been sensitized by direct exposure of the cells in vitro, or cells which have been sensitized by any other suitable means. Isolated antibody producing cells are fused with myeloma cells using procedures which are well-known in the subject field. A fusion procedure which employs polyethylene glycol or Epstein-Barr virus is preferred. The myeloma cell fusion partners to the antibody producing cells are any cells which are suitable for producing hybridoma cells. This includes myeloma cells which are of similar or dissimilar genetic origin. By way of example, some suitable myeloma cell fusion partners are the murine cell lines P3-X63AgS, X63Ag.653, SP2/0 -Ag14, FO, NSI/ 1-Ag4-1, NSO/1, and FOX-NY, the rat cell lines Y3-Ag1.2.3, YB2/0, and IR983F, and the human cell lines U-266, FU-266, and HFB-1. Hybridoma cells, immortalized by fusion, are selected from the mixture of fused and unfused cells using a suitable selection technique, such as hypoxanthineguanine phosphoribosyl transferase (HGPRT) selection as disclosed in *Monoclonal Antibodies: Principles and Practice* (J. W. Goding, Academic Press, San Diego, 1986), which is hereby incorporated by reference for exemplary purposes. In an alternative method, antibody producing cells may be immortalized using cytomegalovirus or another suitable virus. The resulting hybridoma cells, or cells produced using the alternate method, are screened for a cell that produces a monoclonal antibody which reacts in a first assay with a preparation of a first Staphylococcus organism and in a second assay with a preparation of a second Staphylococcus organism. The first and second assays may be any immunological assays and preferably are binding assays, opsonization assays, clearance assays, or any combination of these assays. The first and second preparations of a Staphylococcus organism may be any preparations of a Staphylococcus organism including intact cells, cells fractionated by chemical or physical means, or cell extracts and is preferably a whole-cell or cell surface extract. It is preferred that the first and second preparations of a Staphylococcus organism are of different serotype or species, and more preferred wherein the first Staphylococcus organism is *Staphylococcus epidermidis* (Hay, ATCC 55133).

The present invention also encompasses the DNA sequence of the gene which codes for the isolated monoclonal antibody. This DNA sequence can be identified, isolated, cloned, and transferred to a prokaryotic cell or a eukaryotic cell for expression by procedures which are all well-known in the subject field. Certain procedures, by way of example, are generally described in *Current Protocols in Molecular Biology* (F. W. Ausubel et al., eds., John Wiley & Sons, 1989), which is hereby specifically incorporated by reference.

It is preferred that monoclonal antibodies of the IgG isotype are made, whether by direct isolation of an IgG producing hybridoma cell or by genetic manipulation. One method for the alteration of the isotype of the monoclonal antibody involves the identification of the DNA sequence which codes for the antigen binding site of the original antibody molecule. This DNA sequence is isolated or chemically synthesized and cloned adjacent to the DNA sequence of the structural portion of a different immunoglobulin molecule which may also be isolated or chemically synthesized. The resulting fusion product expressed from this clone would have the antigen binding ability of the original antibody and the structural portion of the new immunoglobulin gene chosen, in other words, the new isotype.

Also preferred is the method wherein human monoclonal antibodies are made. Purely human monoclonal antibodies are made by the fusion of human antibody producing cells and human myeloma cells. Partly human monoclonal antibodies are made by the utilization of nonhuman fusion partners to human antibody producing cells or human myeloma cells. Nonhuman or partly human antibodies may be made more human by chimerization wherein a nonhuman hybridoma cell is fused with a human cell resulting in a hybridoma which is of dual or triple (or more) genetic origin. Alternatively, a nonhuman or a partly human antibody may be made more human by genetic manipulation. Typically, this requires the cloning or the chemical synthesis of DNA which encodes the amino acids of the antigen binding site. This DNA sequence is cloned or placed adjacent to the DNA sequence which codes for the structural portion of a different antibody or amino acid sequence. In this way it is possible to change the overall antigenic structure of the antibody molecule while retaining the specific antigen binding ability. A murine antibody may be altered to appear antigenically more human. This would be very advantageous to reduce or eliminate a possible deleterious immune response. Furthermore, by placing the DNA sequence of the antigen binding site adjacent to the DNA sequence of another protein, the resulting fusion protein expressed is antigenically targeted. This could be especially useful for targeting antibiotics, complement, or immunological factors. The present invention includes an antigen binding site attached to the structural portion of an antibody molecule or another protein which will react in a first assay with a preparation of a first Staphylococcus organism and in a second assay with a preparation of a second Staphylococcus organism.

Another embodiment of the present invention is a pharmaceutical composition comprising isolated immunoglobulin as herein described (including polyclonal antibodies and monoclonal antibodies), and a pharmaceutically acceptable carrier. Pharmaceutically acceptable carriers may be sterile liquids, such as water and oils, including those of petroleum, animal, vegetable or of synthetic origin such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical carriers are described in *Remington's Pharmaceutical Sciences*, 18th Edition (A. Gennaro, ed., Mack Pub., Easton, Pa., 1990), which is hereby specifically incorporated by reference for exemplary purposes.

The invention also comprises a method of treating a patient infected with or suspected of being infected with a Staphylococcus organism comprising the administration of a therapeutically effective amount of a pharmaceutical composition comprising immunoglobulin, polyclonal antibodies, or monoclonal antibodies, and a pharmaceutically acceptable carrier. A patient may be a human or an animal including the dog, the cat, the cow, the sheep, the pig, the goat, and any other suitable mammal, but is preferably a human. Pharmaceutically acceptable carriers are herein described. A therapeutically acceptable amount is that amount of immunoglobulin which is reasonably believed to provide some measure of relief or assistance in the treatment of a Staphylococcus infection. Such therapy may be primary or supplemental to additional treatment, such as antibiotic therapy, for a Staphylococcus infection, an infection caused by a different agent, or an unrelated disease.

A further embodiment of the present invention is a method of preventing infection of a Staphylococcus organism comprising the administration of a prophylactically effective amount of a pharmaceutical composition, a passive vaccine, comprising immunoglobulin, polyclonal antibodies, or monoclonal antibodies, and a pharmaceutically acceptable carrier, all of which are herein described. Treatment may be systemic or localized. Systemic treatment comprises administration of the pharmaceutical composition by intravenous, intraperitoneal, intracelial, intracorporeal injection, or any other effective method of administration of a prophylactically effective amount. Alternatively, the physiological composition may be given locally. This may also be by injection to the particular area infected such as intramuscularly and also subcutaneously. Localized treatment also comprises the administration of a prophylactically effective amount of immunoglobulin by swabbing, immersing, soaking, or wiping, either directly to a patient or to objects which are to be placed within a patient, such as indwelling catheters, cardiac values, cerebrospinal fluid shunts, joint prostheses, other implants into the body, and any other objects, instruments or appliances which carry a risk of becoming infected with or introducing a Staphylococcus infection into a patient.

Another embodiment of the present invention is isolated antigen. As used herein, isolated antigen means any single antigen, any mixture of different antigens, or any combination of antigens which are separated from one or more different organisms. Isolated antigen may be comprised of proteins, polysaccharides, lipids, glycoproteins, or any other suitably antigenic materials. Preferably, isolated antigen contains proteins, polysaccharides and glycoproteins. Most preferably, isolated antigen contains proteins and glycoproteins. It is also most preferred that isolated antigen be a single purified antigen or a small number of purified antigens which may be proteins, polysaccharides, glycoproteins, or synthetic molecules. Methods of macromolecular purification include filtration, fractionation, precipitation, chromatography, affinity chromatography, HPLC, FPLC, electrophoresis, and any other suitable separation technique. Methods for the purification of proteins are well-known in the art. Preferably, isolated antigen is purified by a method comprising the isolation of a culture of bacterial cells of Staphylococcus, suspending the isolated cells in a mixture comprised of a solution of trichloroacetic acid, stirring the mixture at approximately 4° C., centrifuging the mixture and saving the resulting supernatant, combining the supernatant with an alcohol, incubating the alcohol-supernatant combination at approximately 4° C. to precipitate antigen, and isolating the precipitated antigen. More preferred is a method wherein the bacterial cells utilized are *S. epidermidis* (ATCC 55133). By way of example, a number of protein purification methods are described in *Proteins: Structures and Molecular Properties* (T. E. Creighton, W. H. Freeman and Co., New York, 1984), which is hereby specifically incorporated by reference. Numerous methods for the purification of polysaccharides are well-known in the art. By way of example, some of these methods are described in *Carbohydrate Analysis: A Practical Approach*, 2nd Edition (D. Rickwood, ed., IRL Press, Oxford England, 1984), which is hereby specifically incorporated by reference. Methods for the identification, production and use of synthetic antigens are also well-known in the art. By way of example, a number of these methods are described in *Laboratory Techniques in Biochemistry and Molecular Biology: Synthetic Polypeptides as Antigens* (R. H. Burden and P. H. Knippenberg, eds., Elsevier, New York, 1988), which is hereby specifically incorporated by reference.

Isolated antigen, upon introduction into a host, generates an antibody, which may be polyclonal or monoclonal, which reacts in a first assay with a preparation of a first Staphylococcus organism and in a second assay with a preparation of a second Staphylococcus organism. The first and second preparations of a Staphylococcus organism may be any preparations of a Staphylococcus organism including intact cells, cells fractionated by chemical or physical means, or cell extracts and is preferably a whole-cell or cell surface extract. Preferably, the first and second Staphylococcus organisms are of different serotypes or of different species. It is also preferred that one preparation is from *S. epidermidis* (Hay, ATCC 55133). A preparation of a Staphylococcus organism is comprised of polysaccharides, proteins, lipids and other bacterial cell components. It is preferred that the preparation is a polysaccharide and protein preparation, i.e., a preparation that predominantly contains mixtures or combinations of polysaccharides, proteins and glycoproteins. A suitable preparation may be prepared by isolating a culture of bacterial cells of *Staphylococcus epidermidis* (Hay, ATCC 55133), suspending the isolated cells in a mixture comprised of a solution of trichloroacetic acid, stirring the mixture at approximately 4° C., centrifuging the mixture and saving the resulting supernatant, combining the supernatant with an alcohol, preferably absolute ethanol, incubating the alcohol-supernatant combination at approximately 4° C. to precipitate a preparation, and isolating the precipitated preparation.

The first and second assays may be any immunological assays and preferably are binding assays, opsonization assays, clearance assays, or any combination of these assays. One preferred method employs a binding assay, which is herein described, wherein isolated antigen generated antibody is reacted in a binding assay with a preparation of a Staphylococcus organism. The binding assay is preferably an ELISA, or a RIA, but may also be an agglutination assay, a coagglutination assay, a colorimetric assay, a fluorescent binding assay, or any other suitable binding assay. It may be performed by competitive or noncompetitive procedures with results determined directly or indirectly. Another preferred method employs an in vitro opsonization assay which may be a colorimetric assay, a chemilumenescent assay, a fluorescent or radiolabel uptake assay, a cell mediated bactericidal assay, or any other appropriate assay which measures the opsonic potential of a substance. A preferred opsonization assay is the cell mediated bactericidal assay which is herein described. The opsonization assay may use antibody, which may be polyclonal or monoclonal, that has been generated by isolated antigen. In this case, the assay would measure the opsonic activity of the generated antibody, thus providing an indirect determination of the opsonizing potential of isolated antigen.

Another preferred method of identifying immunoglobulin for the treatment of a Staphylococcus infection employs a clearance assay. A preferred clearance assay is conducted in an animal model which has been described herein. A particularly useful animal model comprises the steps of administering a pharmaceutical composition, an immune suppressant, and a Staphylococcus organism to an immature animal, and evaluating whether the pharmaceutical composition reduces mortality of the animal or enhances clearance of the Staphylococcus organism from the animal. The pharmaceutical composition may comprise isolated antigen or antigen generated antibody, which may be polyclonal or monoclonal. When the pharmaceutical composition comprising isolated antigen is administered to the animal, the assay measures the effect of isolated antigen on the animal's own immune system. When the pharmaceutical composition comprising the generated antibody is administered, the assay measures the effect of the administered antibody. This assay may use any immature animal including the rabbit, the guinea pig, the mouse, the rat, or any suitable laboratory animal. The suckling rat is most preferred.

Another preferred embodiment of the present invention is a vaccine comprised of isolated antigen and a pharmaceutically acceptable carrier which, upon introduction into a host, generates an antibody which is protective against infection by a Staphylococcus organism. A pharmaceutically acceptable carrier is herein described. Isolated antigen is herein described and is any single antigen, any mixture of different antigens, or any combination of antigens which are separated from one or more different organisms. Vaccinations would be particularly of benefit to those individuals who are known to be or suspected of being at risk of Staphylococcus infection. This includes patients who are preparing to undergo surgery which involves breakage or damage of skin or mucosal tissue, certain health care workers, and patients whose immune systems are expected to become impaired from some form of therapy such as chemotherapy or radiation therapy for the treatment of cancer.

A further embodiment of this invention comprises a method of treatment with this pharmaceutical composition. A method of treating a human, or any animal, infected with or suspected of being infected with a Staphylococcus organism, comprises the administration of a therapeutically effective amount of the pharmaceutical composition. A method of preventing infection of a Staphylococcus organism in a human, or any animal, comprises the administration of a prophylactically effective amount of the pharmaceutical composition. In either situation, administration of the pharmaceutical composition may involve single or multiple doses given systemically to the entire individual. Administration may be by injection, such as intravenous, intraperitoneal or subcutaneous. Methods for the therapeutic and prophylactic administration of pharmaceutical compositions are well-known in the art or may be determined with a reasonable degree of experimentation. A number of examples are described in *The Pharmaceutical Basis of Therapeutics*, 8th Edition (A. G. Goodman et al., editors, Pergamon Press, New York, 1990), which is hereby specifically incorporated by reference.

A still further embodiment of the present invention is a method for evaluating the efficacy of a pharmaceutical composition used to treat an infectious agent comprising the steps of administering the pharmaceutical composition, an immune suppressant, and an infectious agent to an immature animal, which is preferably a suckling rat, and evaluating whether the pharmaceutical composition reduces mortality of the animal or enhances clearance of the infectious agent from the animal. This method may be used wherein the infectious agent is selected from the group consisting of a bacterium, preferably a gram positive bacterium, a parasite, a fungus and a virus. An immune suppressant is any substance which will impair the immune system of the animal to which it is administered and is selected from the group consisting of steroids, anti-inflammatory agents, prostaglandins, cellular immune suppressants, iron, silica, particles, beads, lipid emulsions and any other effective immune suppressant. Preferably, the immune suppressant is cyclosporin, dexamethasone, triamcinolone, cortisone, prednisone, ibuprofen or any other related compound or combination of compounds. More preferably the immune suppressant is a lipid emulsion, and the lipid emulsion of choice is intralipid. The pharmaceutical composition is preferably administered prophylactically to evaluate the efficacy of the pharmaceutical composition in enhancing resistance to an infectious agent, or therapeutically to evaluate the efficacy of the pharmaceutical composition in directly killing the infectious agent or enhancing the immune response of an infected animal to fight off the infection.

A still further embodiment of the present invention is a diagnostic aid for the detection of a Staphylococcus infection and methods for the use of the diagnostic aid. The diagnostic aid comprises immunoglobulin which may be polyclonal or monoclonal antibodies, or isolated antigen, and a sample of biological fluid containing or suspected of containing antigen or antibody to Staphylococcus. A method for the detection of a Staphylococcus infection in an animal comprises the addition of a biological sample containing or suspected of containing antibody which is specific for Staphylococcus, with isolated antigen, and determining the amount of binding of the antibody to the isolated antigen. Alternatively, this method comprises a biological sample containing or suspected of containing Staphylococcus antigen, and immunoglobulin which is specific to a preparation of a Staphylococcus organism. The immunoglobulin comprises polyclonal or monoclonal antibody, but is preferably a monoclonal antibody. Either method may be an ELISA, a RIA, a colorimetric assay, an agglutination assay, or any other suitable detection assay. It may be performed with competitive or noncompetitive assays using direct or indirect detection procedures. Examples of such methods are disclosed in *Immunology: A Synthesis* (E. S. Golub, Sinauer Assocs., Inc., Sunderland, Mass., 1987), which is hereby specifically incorporated by reference.

A further object of the present invention is a method for the detection of a pharmaceutical composition in a biological sample. When the pharmaceutical composition comprises immunoglobulin, the method comprises the addition of a biological sample containing the pharmaceutical composition with isolated antigen, and determining the amount of binding of the pharmaceutical composition to the isolated antigen. Alternatively, when the pharmaceutical composition comprises isolated antigen, this method comprises the addition of a biological sample containing the pharmaceutical composition with an antibody specific for the pharmaceutical composition, and determining the amount of binding of the pharmaceutical composition to the antibody. These methods may be used, inter alia, to determine the half-life, follow the route of distribution and identify breakdown products of a particular pharmaceutical composition. With this information, better care can be provided by determining the best course of treatment with that pharmaceutical composition.

EXAMPLE 1

One object of the present invention is the identification of immunoglobulin which is reactive in an assay with a preparation of a first Staphylococcus organism and with a preparation of a second Staphylococcus organism. IgG fractions of standard intravenous immunoglobulin (IVIG) were used in these experiments to represent large immunoglobulin pools. Preparations of various pools of IgG from several companies were analyzed for comparison (Gamimmune, Cutter Labs., Inc., Berkeley, Calif.: Sandoglobuin, Sandoz, East Hanover, N.J.; Gammagard, Hyland, Los Angeles, Calif.; Polygam, American Red Cross, Washington, D.C.).

Samples from each of these pools and one sample from an individual patient (SAM), were tested for binding in an enzyme immune assay, specifically an enzyme-linked immunosorbent assay (ELISA), against a preparation of S. epidermidis. Although any S. epidermidis strain could be used, these experiments used Hay, a clinical strain isolated from the blood of a child with S. epidermidis sepsis. This strain is on deposit at the American Type Culture Collection (ATCC) and has been assigned number 55133. Briefly, a culture of S. epidermidis (Hay, ATCC 55133) was grown to log phase (18–36 hours) at 37° C. in 1600 ml aliquots of tryptic soy broth (Difco Labs., Detroit, Mich.). The culture was centrifuged at 5000 rpm for 10 minutes and the cell buttons resuspended in a small volume (10–25 mls) of 2% trichloroacetic acid (TCA) at pH 2.0. The TCA suspensions were combined and stirred overnight at 4° C. The next day, the combined suspension was centrifuged at 5000 rpm for 10 minutes, the supernatants aspirated and saved, and the cell buttons discarded. Supernatants were combined with four volumes of absolute ethanol and stored overnight at 4° C. This solution was centrifuged at 2500 rpm for 10 minutes, the supernatants aspirated and discarded, and the antigen precipitates resuspended in saline and cultured to ensure sterility. Saline suspensions were lyophilized and stored at 4° C. TCA antigen for ELISA testing was made from each serotype by dissolving 1.0 mg of lyophilized extract in 40 mls of coating buffer. Coating buffer was prepared by combining 1.59 g $Na_2CO_3$, 2.93 g $NaHCO_3$, and 0.2 g $NaN_3$ and adding distilled water to a final volume of 1000 mls. This solution was adjusted to a pH of 9.6. One hundred microliter aliquots of the antigen-containing solution were added to each well of 96-well microtiter plates utilizing separate plates for each serotype. Plates were incubated overnight at 4° C., after which, wells were emptied and rinsed four times with PBS-Tween. PBS-Tween was prepared by combining 8.0 g NaCl, 0.2 g $KH_2PO_4$, 2.9 g $Na_2HPO_4$, 0.2 g KCl, 0.2 g $NaN_3$, and 0.5 mls of Tween-20 and adding distilled water to a final volume of 1000 mls. The solution was adjusted to a pH of 7.4. Samples of 100 uls from each pool of immunoglobulin were added to wells. Plates containing antisera were incubated at 4° C. for two hours, after which, they were again emptied and rinsed four times with PBS-Tween. A 1/400 dilution of stock alkaline phosphatase-conjugated goat anti-rabbit IgG (Sigma Chem. Co., St. Louis, Mo.) was prepared in PBS-Tween. Aliquots of 40 uls were added to each well of the microtiter plates and the plates were incubated for two hours at 4° C. The plates were again emptied and rinsed four times with PBS-Tween. A 1 mg/ml solution of p-nitrophenyl phosphate (Sigma Chem. Co., St. Louis, Mo.) was prepared in diethanolamine buffer and 100 ul aliquots of this solution were added to each well of the microtiter plates. Diethanolamine buffer was prepared by combining 97 mls diethanolamine and 0.2 g $NaN_3$, and adding distilled water to a final volume of 1000 mls. The solution was adjusted to a pH of 9.8. These plates were incubated at 37° C. for two hours. Absorbence was measured at 405 nm using the Multiskan® MCC/ 340 instrument (Flow Labs., Lugano, Switzerland).

TABLE I

| Antigen Binding Activity of Human Immunoglobulin for Staphylococcus epidermidis (ATCC 55133) | |
|---|---|
| Immunoglobulin | Optical Density |
| 0609 | 0.707 |
| 163 | 0.731 |
| 0224 | 0.648 |
| 40R07 | 1.014 |
| 110 | 0.786 |
| 2801 | 0.666 |
| 40R09 | 1.026 |
| 069 | 0.901 |
| SAM | 1.002 |

As indicated in Table I, there was a marked difference in the binding activity of each pool tested. Most samples contained low levels of antibody to S. epidermidis. Interestingly, a sample with one of the lowest activities (2801) and the sample with the highest (40R09) are both from the same source, Cutter Laboratories. Among the higher binding pools, 069 and 40R09 were obtained from separate companies. This data indicates that no single method of immunoglobulin preparation can ensure the presence of a high titer of antibody to S. epidermidis, despite the fact that each of the tested pools represent very large collections of human sera. Variations in the content of reactive antibody occurred between preparations prepared by the same company and between lots of the same preparation indicating that all immunoglobulin pools are distinct and that differences in the content of a specific-identifiable antibody can be striking.

EXAMPLE 2

In a second immunoglobulin binding study, random samples of plasma from almost one hundred human patients were screened in an ELISA. Antibody titers to four different strains of S. epidermidis were determined. One strain was obtained from the American Type Culture Collection, Rockville, Md. (ATCC 31423; Serotype I). Two others (Serotypes II and III) were provided by Dr. Y. Ichiman of the St. Marianna University School of Medicine, Japan, and have been previously described (Y. Ichiman, J. Appl. Bacteriol. 56:311 (1984)). Preparations of each were prepared as before. The ELISA was performed as previously described except that 40 uls of each sample were used. As shown in FIG. 1, a significant number of samples contained antibody to each strain of S. epidermidis including the clinical strain, Hay (ATCC 55133). This data indicates that although there was a great deal of variability in binding, there may be cross-reacting antibodies within a single sample.

EXAMPLE 3

To rule out the possibility that the samples of FIG. 1 simply contained large numbers of distinct and strain-specific antibodies to *S. epidermidis*, rabbits were immunized with either a heat-killed whole cell or a TCA prepared vaccine of a preparation of *S. epidermidis*. TCA treated preparations of *S. epidermidis* were prepared as described. One milligram of this preparation was dissolved in 1.0 ml of normal saline, and administered intramuscularly to New Zealand White rabbits. Following a one week rest, a second 1.0 ml dose was given. A final dose given one week later completed the primary immunization series. An identical third (P3), fourth (P4), or fifth (P5) course of immunization can be included and additional booster series as above may be used to further elevate specific antibody levels. Further booster immunizations were given at additional intervals.

The whole bacterial cell vaccine was prepared as follows. Tryptic soy broth was inoculated with *S. epidermidis* (Hay, ATCC 55133) and incubated for three hours at 37° C. A 20 ml aliquot of this preparation was centrifuged at 3000 rpm for 10 minutes, the supernatant discarded, and the cell pellet resuspended in normal saline. A second washing with saline was carried out following a repeat centrifugation and the final suspension was prepared in saline so as to yield a total volume of 10 mls. The bacteria were heated to 56° C. for 60 minutes to produce the heat killed whole cell vaccine which was cultured to ensure sterility. One milliliter (about $10^9$ cells) of this whole cell preparation was administered intravenously to New Zealand White rabbits daily for five days. After a one week rest, the rabbits were again immunized daily for five days. An identical third (P3), fourth (P4), or fifth (P5) course of immunization can be included and additional booster series as above may be used to further elevate specific antibody levels. Further booster immunizations were given at additional intervals.

Sera obtained after immunization with the whole cell preparation showed a marked increase in antibodies to *S. epidermidis*, while the overall magnitude of the immune response was reduced in serum obtained after TCA antigen immunization (FIGS. 2 and 3). However, both the TCA treated sera and the whole cell treated sera produced broadly reactive antibodies to all three serotypes of *S. epidermidis* plus the vaccine strain. As there was only a single strain to which these animals were originally exposed, and there was an equivalent background level of binding before immunization, it is clear that both preparations of *S. epidermidis* (Hay, ATCC 55133) produced antibodies reactive with multiple *S. epidermidis* serotypes.

EXAMPLE 4

All antibodies, even those directed against a given organism, may not enhance immunity and provide enhanced protection from infection. Stated differently, antibodies which bind to an antigen may not necessarily enhance opsonization or clearance of that antigen from the infected animal. Therefore, a neutrophil mediated bactericidal assay was used to determine the functional activity of antibody to *S. epidermidis*. Neutrophils were isolated from adult venous blood by dextran sedimentation and ficoll-hypaque density centrifugation. Washed neutrophils were added to round-bottomed wells of microtiter plates (approximately $10^6$ cells per well) with approximately $3 \times 10^4$ mid-log phase bacteria (*S. epidermidis* Hay, ATCC 55133). Newborn rabbit serum (10 uls), screened to assure absence of antibody to *S. epidermidis*, was used as a source of active complement. Forty microliters of immunoglobulin (or serum) were added at various dilutions and the plates were incubated at 37° C. with constant, vigorous shaking. Samples of 10 uls were taken from each well at zero time and after 2 hours of incubation. Each was diluted, vigorously vortexed to disperse the bacteria, and cultured on blood agar plates overnight at 37° C. to quantitate the number of viable bacteria. Controls consisted of neutrophils plus complement alone. Results are presented as percent reduction in numbers of bacterial colonies observed compared to control samples.

TABLE II

Opsonic Activity of Pools of Human Immunoglobulin for *Staphylococcus epidermidis* (ATCC 55133)

| Immunoglobulin | Opsonic Activity (Percent) |
| --- | --- |
| 0609 | 18 |
| 163 | 8 |
| 0224 | 54 |
| 40R07 | 92 |
| 110 | 12 |
| 2801 | 45 |
| 40R09 | 90 |
| 069 | 15 |
| 2926 | 0 |
| 004 | 54 |
| 100 | 3 |
| 2807 | 23 |
| SAM | 97 |
| control* | 0 |

(* = neutrophil plus complement alone)

Opsonic activity varied from 0% to 23% with some samples and from 90% to 97% with others. As was observed in the binding assay, no correlation could be drawn between preparative techniques used and functional activity observed. However, some of the immunoglobulin which had a high degree of binding in Table I (O.D.>1.0), also had a high level of opsonic activity in Table II (e.g., 40R07, 40R09 and SAM). In other words, only some of the immunoglobulin that bound to TCA treated preparations of *S. epidermidis* promoted phagocytosis and killing of *S. epidermidis*. Thus, for the first time using in vitro screening assays, one could select for immunoglobulin which contains high levels of antibodies for *S. epidermidis* that would also have reliable levels of antibody to prevent and treat *S. epidermidis* infections.

EXAMPLE 5

It was important to determine if the opsonic antibodies for *S. epidermidis* were specifically directed against serotype specific *S. epidermidis* antigens or if they were directed against common staphylococcal antigens. To investigate these alternatives, selected high-titer immunoglobulin was preabsorbed with a preparation of *S. epidermidis* (Hay, ATCC 55133) and tested for opsonic activity against three different gram positive cocci. Absorbing bacteria were grown overnight on blood agar plates, scraped from the plates, suspended in normal saline, and pelleted in 0.5 ml microfuge tubes to one-fifth the volume of the tube. After adding 0.4 mls of immunoglobulin to each; the tubes were vortexed and rotated at a slow speed on an end-over-end tumbler (Fisher Scientific Co., Pittsburgh, Pa.) at 4° C.

overnight. Bacteria were sedimented the following day in a microfuge tube and the supernatant was removed and filtered through a 0.2 um membrane filter. The sterile immunoglobulin contained no detectable *S. epidermidis* binding antibodies and was used either directly or after storage at 70° C.

Selected high-titer immunoglobulin (directed immunoglobulin) showed opsonization of the two species of Staphylococcus and the one species of Streptococcus tested (FIG. 4). With selected immunoglobulin which has been preabsorbed with a preparation of *S. epidermidis*, opsonic activity to *S. epidermidis* was completely removed (95% to 0% bactericidal activity). However, opsonic activity against *Streptococcus agalactiae*, a different genus, was not diminished (93% to 94%). Surprisingly, opsonic activity of *S. aureus* (kindly provided by Dr. Mendiola of the Walter Reed Army Medical Center), which was present in the selected immunoglobulin at about half the level as antibody activity to *S. epidermidis*, was reduced also suggesting that there are antibodies to antigens shared by *S. epidermidis* and *S. aureus*. Therefore, this selected immunoglobulin preparation promoted opsonization by common anti-staphylococcal antibodies that could be identified by absorption with *S. epidermidis*. In the absence of antibody, there was no bactericidal activity demonstrated against any of the bacteria (neutrophil plus complement alone). Thus, it can be concluded that anti-staphylococcal antibodies were directed against key staphylococcal antigens which could provide both specific protection against *S. epidermidis* and broad protection against other Staphylococcus serotypes and species.

EXAMPLE 6

Opsonic activity of serum from rabbits immunized with the TCA prepared and the whole cell preparation was determined. Rabbits were immunized with either the TCA treated or the whole cell preparation of *S. epidermidis* (Hay, ATCC 55133). Sera was collected as before and tested for opsonizing activity against three different serotype strains of *S. epidermidis* plus the vaccine strain in the neutrophil mediated bactericidal assay. As shown in FIGS. 5 and 6, both the TCA treated and whole cell preparations induced an antibody response with very high opsonic activity against all three serotypes. Although pre-vaccinated serum using the TCA treated preparation did show some activity against serotype I (FIG. 5), opsonizing activity nearly doubled after inoculation indicating that staphylococcal common antibodies were indeed responsible. These data show that antibodies to *S. epidermidis* capsular antigens are important for immunity and that one or more antigens may be antigenically similar between different serotypes.

EXAMPLE 7

The opsonizing activity of vaccinated rabbit sera was again determined using *S. aureus* type 5 as the test bacterium (FIG. 7). Overall opsonizing activity against *S. aureus* was not as high as activities observed against strains of *S. epidermidis*, but serum samples from immunized animals did provide significant activity compared to unvaccinated samples. This data indicates that opsonizing antibodies to *S. epidermidis* are also protective against *S. aureus* and again suggests that theses antibodies may be directed against one or more staphylococcal common antigens.

EXAMPLE 8

Many bacteria such as *S. epidermidis* are not pathogenic in normal humans. However, in infants with an immature immune system and in those individuals with an impaired immune system *S. epidermidis* can cause sepsis and even death. Therefore, in any animal model of sepsis it is critical to include these factors. It has been determined that by utilizing an animal with an immature immune system and subjecting that animal to immunological suppressant, the situation observed with septic human patients can be studied. The suckling rat model has proven most useful for these studies and is the preferred animal model. Normal baby rats injected with *S. epidermidis* become bacteremic within two hours and begin to slowly clear the infection shortly thereafter.

TABLE III

*Staphylococcus epidermidis* Bacteremia Levels in Suckling Rats Treated with Normal Saline

| Time Post Infection | Number Bacteremic | Percent Bacteremic | Bacteremia Level |
|---|---|---|---|
| 2 hours | 8/8 | 100 | $3.8 \times 10^2$ |
| 4 hours | 7/8 | 87.5 | $1.3 \times 10^2$ |
| 6 hours | 8/8 | 100 | $7.5 \times 10^2$ |
| 14 hours | 6/8 | 75 | $8.8 \times 10^1$ |
| 18 hours | 3/8 | 37.5 | $0.5 \times 10^1$ |
| 22 hours | 0/8 | 0 | 0 |

All of the animals cleared bacteremia within 72 hours after infection (Table III), suggesting that under normal circumstances, neonatal immunity, while impaired, can eventually control *S. epidermidis*. However, some studies in rats infected with *S. epidermidis* shortly after birth have demonstrated that a lethal infection can still develop (data not shown).

EXAMPLE 9

The effect of intralipid on *S. epidermidis* mortality in suckling rats was assayed. Wistar rats were injected with intralipid, an immune suppressant, just after birth. Animals were administered intralipid beginning on day two of life. Two doses were administered each day for two days. With the final dose of intralipid, animals were also given selected immunoglobulin or saline. After this final dose the animals were infected by subcutaneous injection with a preparation of *S. epidermidis* (Hay, ATCC 55133). Blood samples were subcultured onto plates to ensure that bacteremia was caused by Staphylococcus and to follow clearance after therapy. All animals were followed for five days to determine survival.

TABLE IV

Animal Model: The Effect of Intralipid Dose on *Staphylococcus epidermidis* Mortality in Suckling Rats

| | Survival | | | |
|---|---|---|---|---|
| Intralipid Dose | Infected | | Control | |
| 4 gm/kg | 10/10 | 100% | 7/7 | 100% |
| 8 gm/kg | 10/13 | 76% | 9/9 | 100% |
| 12 gm/kg | 7/12 | 58% | 11/11 | 100% |
| 16 gm/kg | 6/13 | 46% | 11/11 | 100% |
| *16 gm/kg | 2/6 | 33% | 5/5 | 100% |

* = Intralipid dose started on day one of life with infection after final dose on day two.

Animals receiving only *S. epidermidis* successfully overcame infection and survived. Only those animals which were treated with intralipid prior to infection showed a marked decrease in their ability to resist *S. epidermidis*. Death occurred with an increased frequency which correlated with an increased dose of intralipid.

EXAMPLE 10

The effectiveness of selected high-titer (directed) immunoglobulin in providing protection against a lethal infection of *S. epidermidis* (Hay, ATCC 55133) was determined in the suckling rat model. Two day old Wistar rats were given two, 0.2 ml intraperitoneal injections of 20% intralipid. The next day, animals were again given the same series of injections of 20% intralipid plus immunoglobulin or serum from vaccinated animals. After the last injection, approximately $5 \times 10^7$ cells of *S. epidermidis* (Hay, ATCC 55133) were injected subcutaneously at the base of the tail. Mortality was determined for five days.

TABLE V

Effectiveness of Immunoglobulin Directed Against
*Staphylococcus epidermidis* in Providing
Protection from Lethal Infection

| Immunoglobulin | Treated | Died | Mortality |
|---|---|---|---|
| Exp. #1 | | | |
| 40R09 | 24 | 0 | 0% |
| Standard Control | 20 | 4 | 20% |
| untreated | 13 | 7 | 54% |
| uninfected | 11 | 0 | 0% |
| Exp. #2 | | | |
| 40R09 | 13 | 2 | 8% |
| Vaccine Induced | 11 | 2 | 18% |
| Control - saline | 19 | 11 | 42% |

Directed immunoglobulin, selected for the ability to bind to or opsonize a preparation of *S. epidermidis* (lot No. 40R09), provided complete protection from lethal infection in an immunity impaired animal model. These results are identical to the results obtained from uninfected animals. Unselected low-titer immunoglobulin (also called standard immunoglobulin) demonstrated 20% mortality and other controls were as expected. Untreated and uninfected animals had greater than 50% mortality. In a second, similar experiment, directed high-titer human immunoglobulin and vaccine induced high-titer rabbit serum, both strongly protective, produced nearly identical results, whereas a saline control had over 40% mortality. Overall, these data suggest that it is indeed the antibodies directed against *S. epidermidis* which are protective in the suckling rat model.

EXAMPLE 11

Immunoglobulin which bound to a preparation of *S. epidermidis* in an ELISA assay and opsonized *S. epidermidis* organisms in the cell mediated bactericidal assay (directed immunoglobulin) was tested for its capacity to promote clearance of *S. epidermidis* in the suckling rat model. Blood samples were taken from infected animals at regular intervals (FIG. 8). Only directed immunoglobulin which had been previously identified in an ELISA or an opsonic assay decreased levels of bacteria over the course of treatment and it was these animals that showed increased survivals in Table V. Immunoglobulin which did not opsonize or bind to a preparation of *S. epidermidis* did not promote clearance of bacteria from the blood of infected animals.

EXAMPLE 12

Antibody to *S. epidermidis* was analyzed for the ability to provide protection against an international geographically diverse group of *S. epidermidis* strains in the suckling rat clearance assay (FIG. 9). Directed immunoglobulin enhanced survival against a clinical isolate from the United States (ATCC 55133), a prototype laboratory strain (ATCC 31423, capsular serotype I) and two distinct Japanese strains (capsular serotypes II and III). Directed immunoglobulin preabsorbed against a preparation of *S. epidermidis* showed, no increase in survival (FIG. 10). Bacterial counts from blood samples taken during the course of this study also showed that directed immunoglobulin rapidly cleared Staphylococcus bacteremia. Rats treated with saline or preabsorbed immunoglobulin had persistent bacteremia and increased mortality (FIG. 11).

To determine if survival was related to functional anti-Staphylococcus activity of antibody, immunoglobulin preparations with various levels of opsonophagocytic bactericidal activity for *S. epidermidis* (directed immunoglobulin) were compared with saline and preabsorbed immunoglobulin (which had no bactericidal activity for *S. epidermidis*). A significant relationship was observed between opsonophagocytic bactericidal activity of antibody and survival in Staphylococcus sepsis (FIG. 12). While saline, standard immunoglobulin, and preabsorbed directed immunoglobulin provided similarly poor protection (each had little or no opsonophagocytic bactericidal antibody), the unabsorbed directed immunoglobulin provided uniformly good survival indicating that the opsonic anti-Staphylococcus antibodies present were associated with survival.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

I claim:

1. An antigen preparation isolated from *Staphylococcus epidermidis* strain Hay ATCC 55133, wherein said preparation generates broadly reactive opsonic antibody which specifically reacts in an assay with *Staphylococcus epidermidis* serotypes I, II and III, and which exhibits opsonic activity greater than 70%.

2. The antigen preparation as claimed in claim 1 which is isolated by a method comprising the steps of:
   a) isolating a culture of the staphylococcus bacterial cells,
   b) suspending the isolated cells in a mixture comprised of a solution of trichloroacetic acid,
   c) stirring the mixture at approximately 4° C.,
   d) centrifuging the mixture and saving the resultant supernatant,
   e) combining the supernatant with an alcohol,
   f) incubating the alcohol-supernatant combination at approximately 4° C. to precipitate antigen, and
   g) isolating the precipitated antigen.

3. A pharmaceutical composition comprising:
   a) the isolated antigen preparation of claim 1; and
   b) a pharmaceutically acceptable carrier.

4. A method for obtaining broadly reactive opsonic immunoglobulin useful for treating a coagulase negative staphylococcus infection comprising the steps of:
 a) immunizing a mammal with the antigen preparation according to claim 1; and
 b) isolating immunoglobulin from said immunized mammal.

5. A method of making polyclonal antibodies for the treatment of a coagulase negative staphylococcal infection comprising the steps:
 a) immunizing a mammal with the antigen preparation according to claim 1; and
 b) collecting serum from the mammal; and
 c) isolating polyclonal antibodies which react with the antigen preparation of claim 1.

6. An in vitro method for diagnosing infection caused by coagulase negative Staphylococcus in a biological fluid, comprising the steps of:
 a) contacting the biological fluid with the isolated immunoglobulin of claim 5 to form an antigen/antibody complex; and
 b) detecting said complex, wherein the presence of said complex indicates infection by pathogenic coagulase-negative Staphylococcus.

7. A purified culture of Staphylococcus organisms, comprising *Staphylococcus epidermidis* strain Hay ATCC 55133.

* * * * *